United States Patent
Fierobe et al.

(10) Patent No.: US 9,441,213 B2
(45) Date of Patent: *Sep. 13, 2016

(54) CONSTRUCTS AND METHODS FOR THE PRODUCTION AND SECRETION OF POLYPEPTIDES

(71) Applicants: Total Marketing Services, Puteaux (FR); Le Centre National De Recherche Scientifique (CNRS), Paris (FR); Université d'Aix-Marseille, Marseilles (FR); L'Institut National des Sciences Appliquées (INSA), Toulouse (FR)

(72) Inventors: Henri-Pierre Fierobe, Marseilles (FR); Florence Mingardon, Pasadena, CA (US); Angélique Chanal-Vial, Marseilles (FR)

(73) Assignees: Total Marketing Services, Puteaux (FR); Le Centre National De Recherche Scientifique (CNRS), Paris (FR); Université d'Aix-Marseille, Marseilles (FR); L'Institut National des Sciences Appliquées (INSA), Toulouse (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/249,065

(22) Filed: Apr. 9, 2014

(65) Prior Publication Data

US 2014/0220656 A1    Aug. 7, 2014

Related U.S. Application Data

(63) Continuation of application No. 13/056,052, filed as application No. PCT/EP2009/059875 on Jul. 30, 2009, now Pat. No. 8,735,133.

(30) Foreign Application Priority Data

Jul. 31, 2008  (EP) ..................................... 08290739
Nov. 28, 2008  (EP) ..................................... 08291120

(51) Int. Cl.
| | | |
|---|---|---|
| C07H 21/00 | (2006.01) | |
| C12P 21/02 | (2006.01) | |
| C12N 1/15 | (2006.01) | |
| C12N 1/21 | (2006.01) | |
| C12N 5/10 | (2006.01) | |
| C12N 9/42 | (2006.01) | |
| C07K 19/00 | (2006.01) | |

(52) U.S. Cl.
CPC ............. *C12N 9/2437* (2013.01); *C12P 21/02* (2013.01); *C07K 2319/00* (2013.01); *C07K 2319/20* (2013.01); *C07K 2319/70* (2013.01); *Y02E 50/16* (2013.01); *Y02P 20/52* (2015.11)

(58) Field of Classification Search
CPC . C12N 9/2437; C12P 21/02; C07K 2319/00; C07K 2319/20; C07K 2319/70
See application file for complete search history.

(56) References Cited

PUBLICATIONS

Pages et al., GenBank accession No. AAC28899, Dec. 5, 2005.*
Craig et al. (2005) Journal of Biotechnology, 121: 165-173.
Fierobe et al. (2002) The Journal of Biological Chemistry, 277(51): 49621-49630.
Fierobe et al. (2005) The Journal of Biological Chemistry, 208(16): 16325-16334.
Mingardon et al. (2005) Applied Environmental Microbiology, 71(3): 1215-1222.
Mingardon et al. (2007) Applied Environmental Microbiology 73(12): 3822-3832.
Mingardon et al. (2007) Applied Environmental Microbiology, 73(22): 7138-7149.
Perret et al. (2004) Journal of Bacteriology, 186(1): 253-257.
Sabathe et al. (2003) Journal of Bacteriology, 185(3): 1092-1096.
International Search Report for International Application No. PCT/EP2009/059875, mailed Dec. 17, 2009.
Written Opinion for International Application No. PCT/EP2009/059875, mailed Dec. 17, 2009.
Taylor et al. (2006), Journal of Bacteriology, 188(11):3849-3861.

* cited by examiner

*Primary Examiner* — Delia Ramirez
(74) *Attorney, Agent, or Firm* — Hunton & Williams LLP

(57) ABSTRACT

Described herein are molecules, constructs and methods for the production and secretion of polypeptides of interest by host cells, preferably bacterial host cells, and more particularly gram positive bacteria. In particular, the present invention is related to a polynucleic acid encoding a fusion protein and to uses thereof for the secretion of heterologous or homologous polypeptides of interest by a bacterial host cell, preferably *Clostridium* bacteria. The present invention further relates to methods and constructs for the production and secretion of heterologous or homologous polypeptides of interest proteins by host cells using such polynucleic acids and fusion proteins.

20 Claims, 6 Drawing Sheets

| Contructs | | Secretion in *C. acetobutylicum* |
|---|---|---|
| CBM-Xc-Coh-48F |  | + |
| CBM-Xc-48F |  | + |
| CBM-Xc-9G |  | + |
| CBM-Xa-9G |  | ++ |
| CBM-Xa-Xa'-9G |  | +++ |

Legend

— Signal sequence    CBM3a of CipC from *C. cellulolyticum*   Xc  X2 module of CipC from *C. cellulolyticum* cohesin of CipC from *C. cellulolyticum*   Catalytic domains of Cel48F / Cel9G   ═══ linker    Dockerin CBM3c of Cel9G   Xa Xa' X2 modules of CipA from *C. acetobutylicum*

CONSTRUCTS AND METHODS FOR THE PRODUCTION AND SECRETION OF POLYPEPTIDES

CROSS-REFERENCE TO RELATED APPLICATIONS

This application is a continuation of U.S. patent application Ser. No. 13/056,352 (now U.S. Pat. No. 8,735,133), filed Jan. 28, 2011, which is the U.S. National Phase of International Application No. PCT/EP2009/059875, filed Jul. 30, 2009, which claims priority to EP Application No. 08291120.7, filed Nov. 28, 2008, and EP Application No. 08290739.5, filed Jul. 31, 2008, each of which are incorporated by reference herein in their entireties.

FIELD OF THE INVENTION

Described herein are molecules, constructs and methods for the production and secretion of polypeptides of interest by bacterial host cells. In particular, the present invention is related to polynucleic acids encoding a fusion protein and to uses thereof for the secretion of a heterologous or homologous polypeptide of interest by a bacterial host cell. The invention further relates to fusion proteins or parts thereof encoded by such polynucleic acid, and vectors and host cells containing said polynucleic acid. The present invention further relates to methods for the production and secretion of heterologous or homologous polypeptides of interest proteins by bacterial host cells using such polynucleic acids and fusion proteins.

BACKGROUND

Secretion of heterologous proteins is a widely used technique in industry. A cell can be transformed with a nucleic acid encoding a heterologous protein of interest to be secreted and thereby produce large quantities of desired proteins. This technique can be used to produce a vast amount of protein over what would be produced naturally. Proteins of interest are proteins with a wide variety of industrial applications, including therapeutic and agricultural uses, as well as use in foods, cosmetics, cleaning compositions, animal feed, etc. Thus, increasing secretion of proteins produced by micro-organism is of general interest.

Advances in cellular and molecular biology have made it possible, in certain cases, to identify a gene encoding a desired protein, to isolate the gene, to insert the gene into a host cell and to express the inserted gene in the host cell to produce the desired protein. Bacteria have been intensively studied as host cells. When bacteria are used as host cells for this heterologous gene expression, a frequently encountered problem is however that most bacterial expression systems produce proteins intracellularly, and it is usually necessary to disrupt the cells to ensure recovery of the products.

The problem may be overcome by having the bacteria secrete the desired protein into the growth medium. One particularly well documented method of directing the secretion of proteins is the use of a secretory signal sequence. When a signal peptide is fused to the amino-terminal end of a heterologous protein, it directs the heterologous protein to the secretory machinery at the cell membrane. The heterologous protein is then translocated across the membrane. Optionally a specific protease, sometimes referred to as "signal peptidase" or "leader peptidase", removes the signal peptide and releases the heterologous protein.

Translocation of proteins into periplasmic space or secretion into their culture media is subject to a variety of parameters. Typically, vectors for secretion of a protein of interest are engineered to position DNA encoding a secretory signal sequence 5' to the DNA encoding the protein of interest. To increase secretion several approaches can be followed: trying several different signal sequences, mutating the signal sequence, or altering the secretory pathway within the host. However, in many cases the amount of heterologous protein secreted when making use of only a signal peptide to ensure secretion is usually very small, and a significant amount of the heterologous protein is often degraded after it is secreted.

*Clostridium* is a genus of Gram-positive bacteria, which is represented by a wide variety of strains. *Clostridium* bacteria are spore-forming anaerobic bacteria. This genus comprises solventogenic Clostridia such as *C. acetobutylicum* that are able to convert various sugars and polysaccharides into acids and solvents, and cellulolytic Clostridia, such as *Clostridium cellulolyticum*, that are able to efficiently degrade cellulose and related plant cell wall polysaccharides. More in particular, *Clostridium* cellulolyticum produces and secretes large cellulolytic complexes called cellulosomes that efficiently degrade cellulose and related plant cell wall polysaccharides. These complexes contain various enzymes which are tightly bound to a large protein devoid of enzymatic activity called "scaffoldin". The binding of the enzymes on the scaffoldin occurs through interaction between cohesion modules on the scaffoldin and complementary dockerin domains on the enzymes. This high affinity interaction between dockerins and scaffoldins has been suggested for biotechnology applications e.g. recombinant protein purification (Craig et al. 2005, J. Biotechnol. 121:165-173).

On the contrary, *C. acetobutylicum* although it contains in its genome contains a large cluster of genes encoding cellulolytic enzymes and a scaffoldin, is not able to grow on crystalline cellulose.

One of the strategies to combine cellulose-degrading activity with solvent production in one organism has been to introduce the genes encoding the cellulosome of *C. cellulolyticum* into *C. acetobutylicum*. Mingardon et al. have demonstrated the production, assembly and secretion of a minicellulosome by *Clostridium acetobutylicum* by co-expressing the Mannanase gene Man5K from *Clostridium cellulolyticum* with the gene cipC1 encoding a truncated scaffoldin also from *C. cellulolyticum* therein (Mingardon et al. Applied Environm. Microbiol. 2005, vol 71(3): 1215-1222).

Several groups have investigated the possibility of increasing or improving the cellulolytic activity of cellulosome complexes by playing with the different modules present therein and combining different types of cellulases in what is referred to as "designer cellulosomes". It was demonstrated that bifunctional and trifunctional designer cellulosomes which include a chimeric scaffoldin with two or three cohesins of divergent specificity and two or three cellulases each bearing a dockerin complementary to one of the cohesins yielded a multiprotein complex with enhanced synergistic activity on recalcitrant substrates such as straw (Fierobe et al. 2002, J. Biol. Chem. 277, 49621-19630; Fierobe et al. 2005, J. Biol. Chem. 280(16):16325-16334). In addition it was found that such cellulosomes could include combinations of bacterial and fungal enzymes (Mingardon et al. 2007, Appl. Environm. Microbiol. 73(12): 3822-3832). In these experiments the cellulosomes were either produced by co-expression of the vectors encoding the different parts of the cellulosome in *Clostridium cellulolyticum* which naturally secretes these proteins or by mixing the recombinantly produced and purified scaffoldins and enzymes in vitro.

Mingardon et al. describes the production of a "covalent cellulosome", which comprises, in a single polypeptide chain, a CBM together with a family 48 and a family 9 catalytic module. This protein was recovered from *E. coli* in which it was overexpressed by breaking the cells in a French press and purifying the recombinant protein using the c-terminal His tag. The covalent cellulosome was found to be significantly less active on Avicel substrate than the corresponding hybrid cellulosomes (Mingardon et al. 2007, Appl. Environm. Microbiol. 73(22):7138-7149).

Cloning of heterologous or homologous genes encoding secreted proteins, and (over)production and secretion of such heterologous or homologous proteins by bacterial cells such as *Clostridium* species other than *C. cellulolyticum* has not been very widely reported up until now, probably as a result of problems encountered with ensuring secretion of recombinant proteins by these hosts.

In view of the above, it is clear that there is a need in the art to improve secretion of proteins by bacterial cells.

SUMMARY OF THE INVENTION

The instant invention aims to provide an approach to produce and secrete heterologous polypeptides of interest by a bacterial cell, more particularly a gram-positive bacterial cell and/or to improve the production and secretion of homologous polypeptides of interest by a gram positive bacterial cell, and in particular in a *Clostridium* bacterium. Also provided herein are novel molecules and constructs useful in the methods of protein secretion provided herein, and methods of making such molecules and constructs.

The present application is at least partly based on the finding of a new method for microbial production and export of a polypeptide of interest which avoids at least some of the problems associated with secretion as enumerated above. The molecules, constructs and methods according to this invention make it possible to (over)produce and secrete polypeptides of interest, by a bacterial cell. In particular, the present invention provides a polynucleic acid encoding a fusion protein, wherein said fusion protein has a carrier domain which has a functional effect on the secretion of the fused polypeptide of interest. More in particular, the inventors have shown a functional effect of a carrier domain of a fusion protein, i.e. the capability of controlling (inducing and/or improving) (extracellular) secretion of a homologous or a heterologous polypeptide of interest by a recombinant host cell, producing said fusion protein. Said carrier domain comprises a carbohydrate binding module (CBM) and a hydrophilic module (X module), typically of a scaffolding protein and, more particularly in combination with a secretion signal peptide ensures (improved) secretion of a polypeptide of interest. As such the present invention thus advantageously also provides for the use of at least a part of a scaffolding protein, and in particular at least the modules including a CBM, a hydrophilic module thereof, in particular in combination with a signal peptide, for controlling secretion in a host cell of a homologous or a heterologous polypeptide of interest fused to said part of the scaffolding protein.

In a first aspect, the invention therefore provides a polynucleic acid encoding a fusion protein consisting of a polypeptide sequence which comprises in this particular order:

a carrier domain comprising at least one carbohydrate binding module (CBM) of a cellulosomal scaffolding protein fused to at least one hydrophilic domain of a cellulosomal scaffolding protein;

at least one peptide linker for linking the carrier domain to the polypeptide of interest, and at least one polypeptide of interest.

In a particular embodiment of the invention said polynucleic acid further comprises an in frame nucleic acid sequence for the secretion of the encoded fusion protein, and preferably said nucleic acid sequence encodes a signal peptide of a cellulosomal scaffolding protein.

Accordingly, the invention provides polynucleic acids encoding a fusion protein consisting of a polypeptide sequence which comprises, and more particularly, in this order:

at least one suitable signal peptide a carrier domain comprising at least one carbohydrate binding module (CBM) of a cellulosomal scaffolding protein fused to at least one X module of a cellulosomal scaffolding protein;

at least one peptide linker for linking the carrier domain to a polypeptide of interest; and at least one polypeptide of interest.

In particular embodiments of the invention the peptide linker comprises a protease cleavage site for the cleavage of said polypeptide of interest from the remaining fusion protein.

In further particular embodiments, the polypeptide sequence comprises two or more X modules, more particularly two X modules.

In another aspect, the invention is directed to the use of a carrier domain as defined herein, more particularly in combination with a signal peptide, for controlling the secretion of a polypeptide of interest, preferably a polypeptide as defined herein, by a host cell.

In another aspect, the present invention relates to a vector comprising a polynucleic acid according to the invention. Preferably a vector is provided wherein the polynucleic acid is under the control of regulatory sequences for expression of the nucleic acid in a bacterial cell.

In yet another aspect, the invention provides a host cell comprising a polynucleic acid or a vector according to the invention.

Accordingly, particular embodiments of the invention relate to recombinant micro-organisms comprising a polynucleic acid encoding a fusion protein consisting of a polypeptide sequence which comprises, more particularly in this order: (1) at least one signal peptide; (2) a carrier domain comprising at least one carbohydrate binding module (CBM), of the type of CBM of a cellulosomal scaffolding protein, fused to at least one X module of a cellulosomal scaffolding protein; (3) at least one peptide linker for linking the carrier domain to a polypeptide of interest; and (4) at least one polypeptide of interest. The micro-organisms of the invention are characterized in that they secrete the polypeptide of interest.

In further particular embodiments, micro-organisms are provided wherein the polynucleic acid encodes a polypeptide sequence which comprises two or more X modules.

In particular embodiments, micro-organisms are provided wherein the polypeptide sequence comprises a signal peptide, which is a signal peptide of a cellulosomal scaffolding protein. Most particularly, the signal peptide is the signal peptide of the CipC scaffolding protein of *C. cellulolyticum*, or the signal peptide of the CipA scaffolding protein of *C. acetobutylicum*.

In particular embodiments, micro-organisms are provided wherein the polypeptide sequence comprises at least one carbohydrate binding module which is a carbohydrate binding module of type-3 a (CBM3a).

In particular embodiments, micro-organisms are provided wherein the polypeptide sequence comprises at least one X module which is the X2 module of the CipC scaffolding protein of *C. cellulolyticum*, or the X2 module of the CipA scaffolding protein of *C. acetobutylicum*.

More particularly, host cells provided according to the present invention are gram-positive bacteria, more particularly members of the class Clostridia. In further particular embodiments, micro-organisms according to the invention are micro-organisms from a *Clostridium* strain selected from the group comprising *C. acetobutylicum* and *C. beijerinckii*.

Micro-organisms according to the invention may comprise one or more nucleic acids, wherein each nucleic acid comprises a sequence encoding one or more polypeptides of interest.

In still another aspect, the invention provides a fusion protein encoded by the polynucleic acid of the invention. In addition the invention also provides a fusion protein which is fused to the signal peptide as defined herein.

The present invention further relates to a method for the production and secretion by a host cell, more particularly a bacterial host cell, even more particularly a *Clostridium* host cell, most particularly a non-cellulolytic *Clostridium* host cell, of at least one heterologous or homologous polypeptide of interest in a biologically active form comprising introducing into said host cell of a polynucleic acid or a vector according to the invention under conditions effective to cause expression of the encoded fusion protein, wherein the encoded fusion protein is secreted by the host cell into the environment of said host cell. During secretion the signal peptide is optionally cleaved from the fusion protein. Optionally, the polypeptide of interest is simultaneously or additionally cleaved from the carrier domain.

Accordingly, in particular embodiments, the invention provides, methods for the production and secretion by a recombinant micro-organism of at least one heterologous or homologous polypeptide of interest comprising introducing into the micro-organism a polynucleic acid encoding a fusion protein consisting of a polypeptide sequence which comprises, more particularly in this order (1) at least one signal peptide; (2) a carrier domain comprising at least one carbohydrate binding module (CBM) of the type of a cellulosomal scaffolding protein, fused to at least one X module of a cellulosomal scaffolding protein; (3) at least one peptide linker for linking the carrier domain to a polypeptide of interest; and (4) at least one polypeptide of interest, under conditions effective to cause expression of the encoded fusion protein, wherein the encoded fusion protein is secreted by the recombinant micro-organism into the environment of the recombinant micro-organism.

A further aspect of the invention encompasses the use of a polynucleic acid, a vector or a host cell according to the invention for the production and secretion of a polypeptide of interest in a biologically active form.

In particular embodiments of the different aspects of the invention, the polypeptides of interest comprise an enzyme such as a plant cell wall degrading enzyme, and preferably a cellulase. Most particularly, the enzyme is a cellulase of *C. cellulolyticum*, such as Cel48F or Cel9G. Additionally or alternatively, the polypeptide of interest comprises a cellulase CelH of *S. degradans* strain 2-40.

In another embodiment, polypeptides of interest according to the invention may comprise a therapeutic protein. Such a therapeutic protein can be but is not limited to a protein selected from the group comprising therapeutic enzymes, cytokines, and antibodies, and preferably cytokines such as IL-2 or TNFα.

In yet another aspect, the invention relates to a pharmaceutical composition for the treatment of cancer comprising one of a polynucleic acid, a fusion protein, a vector, or a host cell according to the invention and at least one pharmaceutically acceptable carrier. More particularly, the pharmaceutical composition comprises a host cell, most particularly a *Clostridium* host cell, expressing the polynucleic acid according to the invention The invention further relates to a polynucleic acid, a fusion protein, a vector, or a host cell according to the invention for use as a medicament.

In addition, the invention is directed to a polynucleic acid, a fusion protein, a vector, or a host cell according to the invention for treating cancer.

In a further aspect, the invention provides methods of treating cancer in a subject in need thereof comprising administering a polynucleic acid, a vector, a host cell or a pharmaceutical composition according to the invention to said subject, and preferably comprising injecting said polynucleic acid, a vector, a host cell or a pharmaceutical composition at a tumor site in said subject. More particularly, the invention provides a method of treating cancer in a subject in need thereof comprising administering a host cell expressing the polynucleic acid according to the invention to said subject. Optionally, said host cell is injected at the tumor site in said subject.

Additional aspects of the present invention will be apparent in view of the detailed description, which follows.

DESCRIPTION OF THE FIGURES

FIG. 1 further indicates the secretion of these constructs by *C. acetobutylicum*.

DETAILED DESCRIPTION OF THE INVENTION

1. General Definitions

Figure 1:
FIG. 1 is a schematic representation of different constructs according to particular embodiments of the invention. These constructs comprise a polypeptide of interest (cellulase Cel48F or Cel9G) fused to a carrier domain and a signal peptide. The carrier domain comprises a carbohydrate binding module (CBM3a) from a cellulosomal scaffolding protein fused to one or two hydrophilic domains (Xc or Xa) originating from a same or different cellulosomal scaffolding protein(s).
Figure 1:
Figure 1:
Figure 1:
Figure 1:
Figure 1:
Figure 1:

As used herein, the singular forms "a", "an", and "the" include both singular and plural referents unless the context clearly dictates otherwise. By way of example, "a cell" refers to one or more than one cells.

The terms "comprising", "comprises" and "comprised of" as used herein are synonymous with "including", "includes" or "containing", "contains", and are inclusive or open-ended and do not exclude additional, non-recited members, elements or method steps.

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less from the specified value, insofar such variations are appropriate to perform in the disclosed invention.

The recitation of numerical ranges by endpoints includes all numbers and fractions subsumed within that range, as well as the recited endpoints.

All documents cited in the present specification are hereby incorporated by reference in their entirety. In particular, the teachings of all documents herein specifically referred to are incorporated by reference.

The present invention is in general directed to polynucleic acids, constructs, molecules and methods for the production and secretion of polypeptides by host cells.

In this context the term "secretion" refers to the extracellular delivery of a polypeptide of interest, i.e. delivery outside a host cell. In particular this means that the polypeptide of interest is released in or accumulates outside the host cell, and for instance in the "environment" wherein said host cell in grown or is present. In the same context, translocation refers to the delivery of a polypeptide of interest into the periplasmic space.

The terms "polypeptide" and "protein" are used interchangeably herein and generally refer to a polymer of amino acid residues linked by peptide bonds, and are not limited to a minimum length of the product. Thus, peptides, oligopeptides, polypeptides, dimers (hetero- and homo-), multimers (hetero- and homo-), and the like, are included within the definition. Both full-length proteins and fragments thereof are encompassed by the definition. The terms also include post-expression modifications of the polypeptide, for example, glycosylation, acetylation, phosphorylation, etc. Furthermore, for purposes of the present invention, the terms also refer to such when including modifications, such as deletions, additions and substitutions (e.g., conservative in nature), to the sequence of a native protein or polypeptide.

The term "peptide" as used herein preferably refers to a polypeptide as used herein consisting essentially of ≤50 amino acids, e.g., ≤45 amino acids, preferably ≤40 amino acids, e.g., ≤35 amino acids, more preferably ≤30 consecutive amino acids, e.g., ≤25, ≤20, ≤15, ≤10 or ≤5 amino acids.

As used herein, the term "heterologous polypeptide" refers to a polypeptide that does not naturally occur in a host cell. The term "homologous polypeptide" refers to a polypeptide native or naturally occurring in a host cell. In one embodiment, the invention includes host cells producing the homologous polypeptide via recombinant DNA technology. A recombinant protein refers to any protein encoded by a polynucleic acid which has been introduced into the host.

The terms "polynucleic acid" and "nucleic acid" are used interchangeably herein and generally refer to a polymer of any length composed essentially of nucleotides, e.g., deoxyribonucleotides and/or ribonucleotides. Nucleic acids can comprise purine and/or pyrimidine bases, and/or other natural, chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted (such as, 2'-O-alkylated, e.g., 2'-O-methylated or 2'-O-ethylated; or 2'-O,4'-C-alkynelated, e.g., 2'-O,4'-C-ethylated) sugars or one or more modified or substituted phosphate groups. For example, backbone analogues in nucleic acids may include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs).

The term "polynucleic acid" further specifically encompasses DNA, RNA and DNA/RNA hybrid molecules, specifically including hnRNA, pre-mRNA, mRNA, cDNA, genomic DNA, gene, amplification products, oligonucleotides, and synthetic (e.g. chemically synthesised) DNA, RNA or DNA/RNA hybrids. The terms "ribonucleic acid" and "RNA" as used herein mean a polymer of any length composed of ribonucleotides. The terms "deoxyribonucleic acid" and "DNA" as used herein mean a polymer of any length composed of deoxyribonucleotides. The term "DNA/RNA hybrid" as used herein mean a polymer of any length composed of one or more deoxyribonucleotides and one or more ribonucleotides.

A nucleic acid can be naturally occurring, e.g., present in or isolated from nature, can be recombinant, i.e., produced by recombinant DNA technology, and/or can be, partly or entirely, chemically or biochemically synthesized. A nucleic acid can be double-stranded, partly double stranded, or single-stranded. Where single-stranded, the nucleic acid can be the sense strand or the antisense strand. In addition, nucleic acid can be circular or linear.

The term "oligonucleotide" as used herein denotes single stranded nucleic acids (nucleotide multimers) of greater than 2 nucleotides in length and preferably up to 200 nucleotides in length, more preferably from about 10 to about 100 nucleotides in length, even more preferably from about 12 to about 50 nucleotides in length. Oligonucleotides can be synthesised by any method known in the art, e.g., by chemical or biochemical synthesis, e.g., solid phase phosphoramidite chemical synthesis, or by in vitro or in vivo expression from recombinant nucleic acid molecules, e.g., bacterial or retroviral vectors.

As used herein, a "recombinant nucleic acid" is a molecule where the nucleic acid molecule which encodes a polypeptide of interest has been modified in vitro, so that its sequence is not naturally occurring, or corresponds to naturally occurring sequences that are not positioned as they would be positioned in a genome which has not been modified.

The term "signal sequence" or "secretory signal sequence" or "secretory signal peptide" or "signal peptide" denote a polypeptide that as a component of a larger polypeptide, directs the larger polypeptide through a secretory pathway of a host cell in which it is synthesized. The larger polypeptide is commonly cleaved to remove the secretory signal peptide during transit through the secretory pathway. Thus, when a signal peptide is fused to the amino-terminal end of a heterologous protein, it directs the protein to the secretory machinery of the host cell. The heterologous protein is then translocated across the membrane and a specific protease, sometimes referred to as "signal peptidase," removes the signal peptide and releases the protein, in the present case a fusion protein according to the invention.

The term "cellulosomal scaffolding protein" or "scaffoldin" as used herein is intended to refer to a scaffolding protein comprised in a cellulosome. "Cellulosomes" are extracellular multi-enzymatic complexes that are present in some cellulolytic micro-organisms and contain multiple copies of enzymes required to break down carbohydrates. In particular, cellulosomes are composed of a scaffolding protein, which is attached to various cellulases, hemicellulases, and pectinases, that work synergistically to degrade complex cell-wall molecules and this complex allows the organisms to degrade plant cell walls very efficiently. The scaffolding proteins bring together the various other proteins in a signaling pathway and allows for their interaction.

The term "protease cleavage site" or "protease target sequence" which is comprised within the sequence of the polypeptide linker as defined herein, refers to an amino acid sequence that can be recognized by specific proteases. Cleavage at this site results in the release of the polypeptide of interest. It should be noted that the linker polypeptide can be any synthetic polypeptide containing a protease cleavage site, so long as cleavage at this site results in removal of the remaining domains from the polypeptide of interest. Suitable protease target sequences which can be used in polynucleic acids encoding fusion proteins as described herein include but are not limited to sequences which can be recognized by serine proteases such as plasmin, thrombin, factor Xa, or trypsin.

As used herein the term "carrier domain" or "carrier module" is intended to refer to a polypeptide sequence to which a functional domain can be fused in accordance with the present invention. The term "functional domain" or "functional module" is used herein to refer to a polypeptide sequence comprising a polypeptide of interest which is to be produced and secreted in accordance with the present invention. Fusion between said carrier domain or and said functional domain may be effected by means of a linker module.

The expression "at least one" in the context of the present invention means at least two, at least three, at least four, at least five, at least six, etc. and up to at least ten, and also includes one.

2. Nucleotide Sequences

In a first aspect, the invention relates to a polynucleic acid encoding a fusion protein for facilitating the production and secretion of a polypeptide of interest by a host cell, preferably a bacterial host cell, as well as various uses thereof. Specifically, it has been found that a polynucleic acid encoding a fusion protein as defined herein allows for the efficient production of polypeptides by a host cell and the extracellular delivery thereof.

In particular embodiments, the invention provides a polynucleic acid encoding a fusion protein consisting of a polypeptide sequence which comprises:
  a carrier domain comprising at least one carbohydrate binding module (CBM) of a cellulosomal scaffolding protein fused to at least one X module or hydrophilic module of a cellulosomal scaffolding protein;
  at least one polypeptide of interest, and
  at least one peptide linker for linking the carrier domain to the polypeptide of interest.

In further particular embodiments, the invention provides a polynucleic acid encoding a fusion protein consisting of a polypeptide sequence which comprises:
  a suitable secretion signal peptide
  a carrier domain comprising at least one carbohydrate binding module (CBM) of a cellulosomal scaffolding protein fused to at least one X module or hydrophilic module of a cellulosomal scaffolding protein;
  at least one polypeptide of interest, and
  at least one peptide linker for linking the carrier domain to the polypeptide of interest.

In particular embodiments, the invention provides a polynucleic acid encoding a fusion protein consisting of a polypeptide sequence which comprises:
  i) at least one suitable secretion signal peptide
  ii) at least one carbohydrate binding module (CBM) of a cellulosomal scaffolding protein,
  iii) at least one X module or hydrophilic module of a cellulosomal scaffolding protein, which is fused to said CBM (i),
  iv) at least one polypeptide of interest,
  v) at least one peptide linker for linking the X module or hydrophilic module (ii) to the polypeptide of interest (iii).

A polynucleic acid encoding a fusion protein as described herein thus in particular embodiments comprises an in frame nucleic acid secretory sequence for directing the encoded fusion protein out of the host cell. Secretion may thus result in the presence or accumulation of the product, i.e. the entire fusion protein (e.g. CBM-X-enzyme) in the environment, e.g. a culture medium, comprising the host cell.

Thus, in a more particular embodiment, the invention provides a polynucleic acid encoding a fusion protein consisting of a polypeptide sequence which comprises:
  a suitable secretion signal peptide
  a carrier domain comprising at least one carbohydrate binding module (CBM) of a cellulosomal scaffolding protein fused to at least one X module or hydrophilic module of a cellulosomal scaffolding protein;
  at least one peptide linker for linking the carrier domain to a polypeptide of interest; and
  at least one polypeptide of interest.

Most particularly, the sequences are arranged in the order they are listed above.

More particularly, the invention provides a polynucleic acid encoding a fusion protein consisting of a polypeptide sequence which comprises:
  i) at least one carbohydrate binding module (CBM) of a cellulosomal scaffolding protein,
  ii) at least one X module or hydrophilic module of a cellulosomal scaffolding protein, which is fused to said CBM (i),
  iii) at least one signal peptide e.g. a signal peptide from a bacterial scaffolding protein
  iv) at least one polypeptide of interest, v) at least one peptide linker for linking the X module or hydrophilic module (ii) to the polypeptide of interest (iii).

Accordingly, the invention provides polynucleic acid sequences comprising individual sequences encoding each of the modules described above operably linked, more particularly covalently linked, such that expression of the polynucleic acid sequences results in a fusion protein as described herein.

Suitable nucleic acids sequences of secretory signal sequences which can be used in polynucleic acids encoding fusion proteins as described herein are described elsewhere herein and include but are not limited to a signal peptide of a cellulosomal scaffolding protein, such as e.g. the signal peptide of the CipC scaffolding protein of *C. cellulolyticum* ATCC 35319 (gene bank U40345), or the signal peptide of the CipA scaffolding protein of *C. acetobutylicum* ATCC 824 (gene bank AE007606 or AE001437).

In particular embodiments the fusion protein as defined herein may be cleaved during secretion, such that secretion results in the presence or accumulation of the polypeptide of interest in the environment, e.g. a culture medium, comprising the host cell. To that end, fusion proteins of the invention can also be engineered to contain a cleavage site to aid in protein recovery. Therefore in particular embodiments the invention provides a polynucleic acid encoding a fusion protein as described herein having a peptide linker comprising a protease cleavage site.

3. Fusion Protein

In another aspect, the present invention relates to a fusion protein that is encoded by a polynucleic acid according to the invention.

The present fusion protein which may also be denoted as a chimeric protein. "Fusion" refers to the joining together of a polynucleic acid encoding a polypeptide of interest and a polynucleic acid encoding a carrier domain comprising one or more modules, in frame. Expression of the joint polynucleic acids results in a chimeric protein also named hereinafter a "fusion protein". The fusion protein of the present invention may comprise an enzymatic or chemical cleavage site upstream and preferably adjacent the N-terminus of the polypeptide of interest and/or an enzymatic or chemical cleavage site downstream and preferably adjacent the C-terminus of the domain provided upstream of the polypeptide of interest thereby providing a means for recovering the polypeptide of interest from the fusion protein through use of a cleaving agent.

In general, a fusion protein according to the invention consists of a polypeptide sequence, which comprises:
 a carrier domain, which preferably comprises at least one carbohydrate binding module (CBM) of a cellulosomal scaffolding protein fused to at least one hydrophilic domain of a cellulosomal scaffolding protein; and
 a functional domain which comprises at least one polypeptide of interest.

More particularly, a fusion protein according to the invention consists of a polypeptide sequence, which comprises:
 a suitable signal peptide sequence
 a carrier domain, which preferably comprises at least one carbohydrate binding module (CBM) of a cellulosomal scaffolding protein fused to at least one hydrophilic domain of a cellulosomal scaffolding protein; and
 a functional domain which comprises at least one polypeptide of interest.

The carrier domain is linked to the functional domain by means of a linker module.

It shall be further noted that in accordance with particular embodiments the present invention, the fusion protein is a protein construct that has been cleaved from and thus does no longer include a signal peptide. In these embodiments, the signal peptide which is fused to the fusion protein is cleaved from said fusion protein during secretion. Optionally, in case the polypeptide linker mentioned above contains protease cleavage site, the polypeptide of interest may be further cleaved from the remaining part of the fusion protein upon action of suitable protease(s), which are able to recognize said protease cleavage site and to cleave the polypeptide sequence at that site. Accordingly, the term "fusion protein" as used herein may refer to either the polypeptide sequence as synthesized within the cell (i.e. comprising the signal sequence) or after secretion, whereby the signal sequence has optionally been released or cleaved therefrom.

The object of the production of polypeptides of interest in the form of fusion proteins according to the invention is to ensure or increase secretion of the polypeptide of interest.

In particular embodiments, the fusion protein of the present invention has particular improved properties, such as e.g. increased activity compared to the isolated polypeptide of interest. For instance, in particular embodiments, for example where the polypeptide of interest is an enzyme, the presence of one or more carbohydrate binding modules and/or one or more hydrophilic modules in the fusion protein may increase the activity of the enzyme compared to the isolated enzyme. Accordingly, in particular embodiments, the invention relates to fusion proteins comprising a carrier domain according to the invention having improved properties compared to the polypeptide of interest.

In alternative particular embodiments, the fusion protein of the activity of the fusion protein is similar or decreased compared to the native polypeptide.

The separate modules comprised in the present fusion protein and parts thereof such as the carrier domain and the functional domain, as defined herein will be discussed into more detail hereunder.

A. Carbohydrate Binding Module

A first module in a carrier domain, or in a fusion protein according to the invention comprises a carbohydrate binding module.

The terms "carbohydrate binding module", "carbohydrate binding molecule"; "carbohydrate binding protein" and "carbohydrate binding domain" are used herein as synonym and refer to a protein or an essential part, or a homologue thereof, which is capable of binding a polysaccharide substrate, such as e.g. cellulose. The Carbohydrate Binding Modules (CBMs) are functionally independent modules, frequently found in nature associated to proteins involved in biomass breakdown. These modules are defined as sequences of amino acids, present in enzymes which act on carbohydrates, exhibiting tri-dimensional structure and carbohydrate binding ability. The carbohydrate binding modules preferably include carbohydrate binding modules of a cellulosomal scaffolding proteins.

The term "essential parts thereof" in this context refers to parts of carbohydrate binding modules which are capable of binding carbohydrates.

The term "homologue" of a carbohydrate binding protein as used herein refers to a protein which has an amino acid sequence that has at least 30% identity, preferably at least 40%, 50%, 60%, 70%, 80% or 90% identity, most preferably at least 95% identity with a functional portion of the amino acid sequence of a carbohydrate binding protein. It should be understood that instead of % "identity", also the corresponding % "similarity" can be used to define homologues according to the invention.

In a particular embodiment, a carrier domain or a fusion protein according to the invention comprises a carbohydrate binding module from a cellulosomal scaffolding protein, as defined above. In further particular embodiments the carrier domain comprises a carbohydrate binding module from an enzyme but which is similar to a carbohydrate binding module from a cellulosomal scaffolding protein (e.g. CBM3b)

In further particular embodiments, a carrier domain or a fusion protein according to the invention comprises a carbohydrate binding module which is a CBM3 module, i.e. a carbohydrate binding type-3 module. Carbohydrate-binding modules have been classified into more than 40 families according to sequence homology. Several cellulolytic enzymes share a conserved region of about 150 amino acid residues, the CBM3 domain. The CBM3 domain has been classified in three different subtypes, termed family IIIa, IIIb and IIIc. In a preferred embodiment, a carrier domain or a fusion protein according to the invention comprises a carbohydrate binding module which is a CBM3 module of type IIIa or IIIb. In further particular embodiments the carrier domain or a fusion protein according to the invention comprises a carbohydrate binding module which is a CBM3 module of type IIIa. The carbohydrate binding modules of family IIIa bind to crystalline cellulose.

Particular examples of carbohydrate binding modules comprised in a carrier domain or a fusion protein according to the invention comprise but are not limited to carbohydrate binding modules of cellulosomal scaffolding proteins selected from the group comprising cellulosome integrating protein A (CipA) of *Clostridium thermocellum* (gene bank X67406 or X67506), cellulosome integrating protein C (CipC) of *Clostridum cellulolyticum* (gene bank U40345), cellulose binding protein A (CbpA) of *Clostridum cellulovorans* (gene bank M73817), and cellulosome integrating protein A (CipA) of *Clostridium acetobutylicum* (gene bank AE007606 or AE001437).

A particular example of a carbohydrate binding module comprised in a carrier domain or a fusion protein according to the invention is the carbohydrate binding module of the scaffolding protein CipC of *Clostridium cellulolyticum* (gene bank U40345). The *C. cellulolyticum* cellulosome is organized around the scaffolding protein CipC, which permits the binding of the different cellulosomal enzymes via interactions of dockerin-cohesin domains.

In a particular embodiment the carbohydrate binding module comprises homologues of the carbohydrate binding module of the scaffolding protein CipC of *Clostridium cellulolyticum*. Therefore, according to a further embodiment, the invention also relates to a carrier domain or a fusion protein as described above, wherein said at least one carbohydrate binding module comprises a polypeptide having at least 30% identity, preferably at least 40%, 50%, 60%, 70%, 80% or 90% identity, most preferably at least 95% identity with the carbohydrate binding module of the scaffolding protein CipC of *Clostridium cellulolyticum*. It should be understood that instead of % "identity", also the corresponding % "similarity" can be used to define homologues according to the invention.

B. X module

Another module of a fusion protein according to the invention comprises at least one X module, more particularly a hydrophilic module, and preferably a hydrophilic module of a cellulosomal scaffolding protein.

The terms "hydrophilic domain", "hydrophilic module" and "X module" are used herein as synonym and refer to a hydrophilic domain of a cellulosomal scaffolding protein. In particular embodiments, the X-module is an X-module of a mesophilic *Clostridium cellulosomal* scaffolding protein.

Thus in particular embodiments, the X module comprised in a fusion protein according to the invention is of bacterial origin, preferably from a bacteria of the genus Clostridia, more particularly a mesophilic clostridia, e.g. from *Clostridium thermocellum*, *Clostridium cellulolyticum*, *Clostridium acetobutylicum*, *Clostridium josui* or *Clostridium cellulovorans*. It shall be noted that X modules found in *C. acetobutylicum*, *C. cellulolyticum*, *C. cellulovorans*, *C. josui* may be referred to as "X2" modules, while X modules found in *C. thermocellum* may be called "X1" modules.

Particular examples of X modules comprised in a carrier domain or a fusion protein according to the invention comprise but are not limited to hydrophilic domains of cellulosomal scaffolding proteins selected from the group comprising cellulosome integrating protein A (CipA) of *Clostridium thermocellum* (gene bank X67406 or X67506), cellulosome integrating protein C (CipC) of *Clostridum cellulolyticum* (gene bank U40345), cellulose binding protein A (CbpA) of *Clostridum cellulovorans* (gene bank M73817), cellulosome integrating protein A (CipA) of *Clostridium josui* (gene bank AB004845) and cellulosome integrating protein A (CipA) of *Clostridium acetobutylicum* (gene bank AE007606 or AE001437).

A particular example of an X module comprised in a carrier domain or a fusion protein according to the invention is the X2 module of the scaffolding protein CipC of *Clostridium cellulolyticum* (gene bank U40345).

Another particularly preferred example of an X module comprised in the fusion protein according to the invention is the X2 module of the scaffolding protein CipA of *Clostridium acetobutylicum* (gene bank AE007606 or AE001437).

In further embodiments, the X-module is a module homologous to the X modules described herein.

In particular embodiments the X module is a homologue of the hydrophilic module of the scaffolding protein CipC of *Clostridium cellulolyticum* or of the scaffolding protein CipA of *Clostridium acetobutylicum*. Therefore, according to a further embodiment, the invention also relates to fusion proteins, nucleic acid sequences encoding them and host cells, more particularly recombinant micro-organisms as described above, wherein said at least one X module comprises a polypeptide having at least 30% identity, preferably at least 40%, 50%, 60%, 70%, 80% or 90% identity, most preferably at least 95% identity with the hydrophilic module of the scaffolding protein CipC of *Clostridium cellulolyticum* or of the scaffolding protein CipA of *Clostridium acetobutylicum*. It should be understood that instead of % "identity", also the corresponding % "similarity" can be used to define homologues according to the invention.

It shall be further noted that in accordance with the present invention the CBM module and the X module applied in a carrier domain or a fusion protein according to the invention may originate from the same or from different cellulosomal scaffolding proteins.

In one particular embodiment, the present invention relates to a polynucleic acid encoding a fusion protein having a carrier domain comprising a carbohydrate binding module (CBM) of a cellulosomal scaffolding protein fused to one X module of a same or a different cellulosomal scaffolding protein. In another particular embodiment, the present invention relates to a polynucleic acid encoding a fusion protein having a carrier domain comprising a carbohydrate binding module (CBM) of a cellulosomal scaffolding protein fused to two of the same or to two different X modules of a same or a different cellulosomal scaffolding protein.

In particular embodiments the fusion protein comprises two X modules, three X modules, or four or more X modules. These may be located in the fusion protein adjacent to each other or separated by one or more other modules of the fusion protein.

C. Signal Peptide

In particular embodiments, the fusion protein, comprising a carrier domain ensuring the secretion of the polypeptide of interest according to the present invention, further comprises a sequence encoding a secretion signal sequence. In the constructs according to these embodiments of invention, this secretion signal sequences is linked to one of the other sequences of the construct, i.e. either the sequence encoding the CBM domain, the X module or the sequence encoding the polypeptide of interest, such that the signal sequence and the polypeptide of interest are operably linked, more particularly covalently linked. In this connection, "operably linked" denotes that the sequence encoding the signal sequence and the sequence encoding the polypeptide to be secreted are connected in frame or in phase, such that upon expression the signal peptide facilitates the secretion of the polypeptide so-linked thereto.

It shall be appreciated that suitable signal sequences may depend on the type of micro-organism in which secretion is desired. For example, distinct signal sequences may be required in different Gram-positive bacteria. By means of example and not limitation, secretion in Gram-positive bacteria, and in particular in *Clostridium* such as *C. acetobutylicum*, may be achieved using the signal sequence of the Cel5A precursor polypeptide of *C. cellulolyticum* (exemplary sequence: Genbank acc. no. AAA51444, seq version 1 revised on Oct. 31, 1994), or of the CipC precursor scaffolding protein of *C. cellulolyticum* (exemplary sequence: Genbank acc. no. AAC28899, seq. version 2 revised on Dec. 5, 2005), or of the CipA precursor scaffolding protein of *C. acetobutylicum* (exemplary sequence: Genbank acc. no. AAK78886, seq. version 1 revised on Jan. 19, 2006).

It shall also be appreciated that native (or homologous, endogenous) signal peptides of polypeptides to be expressed by the micro-organisms as taught herein may be employed, insofar as they are functional in said micro-organisms. Hence, by means of example, secretion of Cel48F or Cel9G of *Clostridium Cellulolyticum* may be achieved using the CipC scaffolding protein of *C. cellulolyticum*. Similarly, secretion of Cel5H or related polypeptides in a heterologous organism may be achieved using the endogenous or homologous secretion signal sequence of the Cel5H precursor polypeptide.

D. Polypeptide of Interest

The present fusion protein or a functional domain thereof according to the invention further comprises a protein of interest to be produced and secreted by constructs and methods as provided herein. The protein which is produced and secreted by a—preferably bacterial—host as defined herein can be any protein of interest. In a preferred embodiment, it is a heterologous protein, i.e. heterologous to the host. Alternatively, the protein is homologous.

The terms "polypeptide of interest" and "protein of interest" are used herein as synonym and refer to a protein that is produced and secreted by a host cell as defined herein.

The present invention is not limited in the type or function of polypeptide of interest that can be produced and secreted in accordance with the present invention. The nature of the protein of interest is determined by the application of the nucleic acids and host cells comprising them.

In one embodiment, said polypeptide of interest is an enzyme, preferably selected from the group comprising but not limited to proteases, reductases, lipases, kinases, phophatases, oxidases, and carbohydrases.

For example, said polypeptide of interest is an enzyme selected from the group comprising but not limited to transferases (EC.2), isomerases (EC.5), oxidoreductases (EC.1) comprising but not limited to enzymes of group EC 1.10.3 including laccase or peroxidases (EC 1.11.1) including ligninase and lignin peroxidase, and hydrolases (EC.3) comprising but not limited to carboxylic ester hydrolases (EC 3.1.1) including hemicellulase, and glycosidases (EC 3.2.1) including endoglucanases, exoglucanases, alpha-amylase, glucoamylase, pectinase, endo-glucosidase H, cellulase, cellobiohydrolase, and endo-processive cellulase.

In particular embodiments said polypeptide of interest is a plant cell wall degrading enzyme. The secretion of such enzymes by micro-organisms is of interest in the context of degradation of plant material, e.g. in the context of biofuel production. The term "plant cell wall degrading enzymes" is used herein to refer to enzymes which catalyze the cleavage of cellulosic or lignocellulosic materials, and include but are not limited to cellulases, hemicellulases, laccases, cellobiohydrolases and other enzymes involved in breaking down cellulose and hemicellulose into simple sugars such as glucose, xylose, arabinose, mannose and galactose.

In a particular embodiment said polypeptide is a cellulase. This term includes processive and non-processive cellulases. Processive cellulase will continue to interact with a single polysaccharide strand, non-processive cellulase will interact once then disengage and engage another polysaccharide strand. Explicitly, but not exclusively, included within the term cellulases are those enzymes which fall under the Enzyme Classification heading EC 3.2.1.4 enzymes, also called β-1,4-endoglucanases, cleave β-1,4-glycosidic linkages randomly along the cellulose chain, EC 3.2.1.91 enzymes also called cellobiohydrolases or exoglucanases which sequentially release cellobiose or glucose from one extremity of the cellulose chain, and EC 3.2.1.4/EC 3.2.1.91 enzymes also called endo-processive cellulases which display a mixed mode of action (both endo and exo glucanase).

According to particular embodiments, the plant cell wall degrading enzymes used in the present invention are of microbial origin, e.g. of fungal or bacterial origin, preferably of bacterial origin, for example from a bacterium of the genus Alteromonadaceae, e.g. *Saccharophagus degradans* strain 2-40, of the genus *Thermomonospora*, e.g., from *T. fusca*, of the genus Cellulomonadaceae e.g. *C. fimi*, of the genus Clostridia, e.g. from *Clostridium thermocellum, Clostridium cellulolyticum, Clostridium acetobutylicum, Clostridium cellulovorans, Clostridium josui*. In another embodiment, plant cell wall degrading enzymes used in the present invention are of fungal origin, for example from a fungus of the genus Neocallimastigomycota, e.g. from *N. patriciarum* or *Orpinomyces* sp strain PC-2.

Particular examples of cellulases suitable for use in a fusion protein or a functional domain thereof according to the invention include but are not limited to:

cellulases of *C. cellulolyticum* selected from the group comprising Cel48F, Cel9G, Cel9R, Cel9P, Cel9E, Cel9H, Cel9J, Cel9M, Cel8C, Cel5N, and Cel5A;

cellulases of *C. thermocellum* selected from the group comprising Cel9D, Cel9J, CBH9A, Cel9H, Cel9K, Cel5E, Cel48S, Cel9F, Cel9N, Cel9Q, Cel5O, Cel5B, Cel5G, Cel8A, Cel5C and Cel9I;

cellulases of *C. acetobutylicum* selected from the group comprising Cel48A, Cel9G, Cel9R, Cel9P, Cel9E, Cel9H, Cel9J, Cel9M, and Cel5A;

cellulases of *S. degradans* strain 2-40 selected from the group comprising Cel9A, Cel9B, Cel5J, Cel5I, Cel5F, Cel5H, Cel5D, Cel5B, Cel9G, Cel5E, Cel5A, Cel5C and Cel6A.

putative cellulases from *Pseudomonas* species ND 137 such as AcIa.

In further particular examples, a cellulase suitable for use in a fusion protein or a functional domain thereof according to the invention includes the cellulases Cel48F or Cel9G of *C. cellulolyticum*.

In further particular examples, a cellulase suitable for use in a fusion protein or a functional domain thereof according to the invention includes the cellulase Cel5H of *S. degradans* strain 2-40.

In further particular embodiments, the polypeptide of interest to be produced and secreted in accordance with the present invention is a therapeutic protein. A "therapeutic protein" as used herein, refers a protein, peptide, glycoprotein or glycopeptide that can be administered to a subject to treat a disease or dysfunction or to improve health of the subject. It includes both molecules which in themselves exert a therapeutic effect and molecules which act on or combine with another molecule to exert a therapeutic effect, such as part of a combination drug or a pro-drug converting enzyme. In particular embodiments the subject is an animal or a human. In a further preferred embodiment, the therapeutic protein is a human protein or an animal protein, e.g. from a rodent, e.g. rat, mice. In another further particular embodiment, the disease or dysfunction includes a cancer. Accordingly, in particular embodiments, the polypeptide of interest is an anti-tumor agent.

In particular embodiments the therapeutic protein is an active protein, e.g., has enzymatic activity, or biological activity, such as binding activity to a ligand or receptor, ability to activate an intracellular signal transduction pathway, or ability to elicit an immune response in a mammal, e.g., a human. The therapeutic protein may be glycosylated or otherwise modified in vitro by one or more glycosyltransferases.

In particular embodiments the protein of interest for use in a fusion protein or a functional domain thereof according to the invention is a therapeutic protein selected from the group comprising therapeutic enzymes, cytokines, and antibodies (including all known forms of antigen-binding molecules). It shall be noted that in accordance with the present invention the term antibodies also includes "catalytic antibodies".

In a further particular embodiment, a therapeutic protein is selected from the group comprising cytokines such as but not limited to IL-2, IL-12, GM-CSF (granulocyte-macrophage colony-stimulating factor), TNF (tumor necrosis factor)-α, etc.

The use of therapeutic proteins is more particularly envisaged for the therapeutic applications of the invention described herein.

In further particular embodiments, the polypeptide of interest is a diagnostic polypeptide, such as an antibody. These may be of interest in the diagnostic use of the host cells of the present invention.

E. Linker Module

A fusion protein according to the invention typically comprises another module, which consists of at least one peptide linker for linking the carrier domain of the protein to the functional domain or the polypeptide of interest.

Preferably the peptide sequence, linking the carbohydrate binding module to the hydrophilic module is a sequence which is known in the art and which can be conveniently found in cellulosomal scaffolding proteins.

Said linker polypeptide preferably comprises a polypeptide of at least 3, preferably at least 4 or 5, most preferably at least 7, and more preferably at least 12 amino acids. Preferably said linker is a polypeptide comprising between 3 and 15 amino acids. Preferably said linker is a polypeptide comprising non-charged amino acids such as glycine, serine, cysteine, asparagine, tyrosine, glutamine, alanine, valine, proline, threonine, and preferably glycine or serine.

Suitable examples of linker polypeptides comprise linker polypeptides found in bacterial cellulosomal scaffolding proteins such as but not limited to CipA of *C. acetobutylicum* (AE007606), CipC of *C. cellulolyticum* (U40345), CipA of *C. thermocellum* (X67406 or X67506), CbpA of *Clostridum cellulovorans* (M73817), CipA of *Clostridium josui* (AB004845).

As mentioned above, a peptide linker as defined herein may comprise a protease cleavage site. Cleavage at this site results in the release of the polypeptide of interest.

4. Vectors

According to a further aspect of the present invention, there are provided expression constructs to facilitate introduction into a host cell and preferably a bacterial cell and/or facilitate expression and/or facilitate maintenance of the polynucleotide sequence encoding a fusion protein according to the invention. The expression constructs may be inserted into a plasmid or a vector, which may be commercially available.

By "vector" is meant a polynucleotide molecule, preferably a DNA molecule derived, for example, from a plasmid, bacteriophage, or plant virus, into which a polynucleotide can be inserted or cloned. A vector preferably contains one or more unique restriction sites and can be capable of autonomous replication in a defined host cell, or be integrable with the genome of the defined host such that the cloned sequence is reproducible. The choice of the vector will typically depend on the compatibility of the vector with the host cell into which the vector is to be introduced.

According to an embodiment of the present invention, the expression construct is an expression vector, suitable for transformation into host organisms, preferably bacteria, and suitable for maintenance and expression of a fusion protein according to the present invention in a transformed host cell.

An "expression vector" is a construct that can be used to transform a selected host cell and provides for expression of a coding sequence in the selected host. Expression vectors can for instance be cloning vectors, binary vectors or integrating vectors. The invention thus also relates to a vector comprising any of the nucleic acids described above. Said vector may further comprise regulatory sequences for controlling expression of the nucleic acid in said host cell. Particularly useful in the practice of this invention are expression vectors that provide for the expression of bacterial cells of nucleic acid encoding a fusion protein as defined herein. In general, expression involves the use of an expression vector that is able to replicate efficiently in a host cell, such that the host cell accumulates many copies of the expression vector and, in turn, synthesizes high levels of a desired product (fusion protein) encoded by the expression vector.

The terms "regulatory sequences" and "control sequence" used herein are to be taken in a broad context and refer to regulatory nucleic acid sequences capable of driving and/or regulating expression of the sequences to which they are ligated (covalently linked) and/or operably, linked. The control sequences differ depending upon the intended host organism and upon the nature of the sequence to be expressed. For expression of a protein in prokaryotes, the control sequences generally include a promoter, a ribosomal binding site, and a terminator. In eukaryotes, control sequences generally include promoters, terminators and, in some instances, enhancers, and/or 5' and 3' untranslated sequences. The term 'control sequence' is intended to include, at a minimum, all components necessary for expression, and may also include additional advantageous components. According to a preferred embodiment of the present invention, the control sequence is operable in a bacterium, and preferably a gram positive bacterium; preferably the control sequence is a sequence derived from a gram positive bacterium. The term "control sequence" encompasses a promoter or a sequence capable of activating or enhancing expression of a nucleic acid molecule in a host cell.

According to one embodiment of the present invention, the expression construct is a bacterial expression vector, suitable for transformation into bacteria and suitable for maintenance and expression of a fusion protein according to the present invention in a transformed bacterial cell. The invention thus also relates to a vector comprising any of the nucleic acids described above. Said vector may further comprise regulatory sequences for controlling expression of the nucleic acid in a bacterial cell.

Expression and cloning vectors usually contain a promoter that is recognized by the host organism and is (covalently and) operably linked to the nucleic acid encoding the polypeptide of interest. Promoters are untranslated sequences located upstream (5') to the start codon of a structural gene (generally within about 100 to 1000 bp) that control the transcription and translation of a particular nucleic acid sequence, such as that encoding a fusion protein as defined herein, to which they are operably linked. Such promoters typically fall into two classes, inducible and constitutive. Inducible promoters are promoters that initiate increased levels of transcription from nucleic acid under their control in response to some change in culture conditions, e.g., the presence or absence of a nutrient or a change in temperature. At this time, a large number of promoters recognized by a variety of potential host cells are well known. These promoters are operably linked to nucleic acid encoding the polypeptide of interest by removing the promoter from the source nucleic acid by restriction enzyme digestion and inserting the isolated promoter sequence into the vector. Both the naturally occurring promoter sequence and many heterologous promoters may be used to direct amplification and/or expression of the polypeptide of interest. In general, plasmid vectors containing promoters and control sequences that are derived from species compatible with the host cell are used with these hosts. The vector ordinarily carries one or more replication sites as well as marker sequences, which are capable of providing phenotypic selection in transformed cells.

Promoters suitable for use with prokaryotic hosts illustratively include the β-lactamase and lactose promoter systems, alkaline phosphatase, the tryptophan (trp) promoter system and hybrid promoters such as the tac promoter. However, other functional bacterial promoters are suitable. Their nucleotide sequences are generally known, thereby enabling a skilled worker operably to ligate them to nucleic acid encoding the protein secretion molecule as defined herein using linkers or adapters to supply any required restriction sites. Promoters for use in bacterial systems. A Shine-Dalgarno sequence should also be operably linked to the nucleic acid encoding the protein secretion molecule as defined herein.

According to one embodiment of the invention, the vectors comprise a constitutive promoter. Examples of constitutive promoters suitable for the constructs and methods according to the present invention include but are not limited to the CaMV35S promoter, GOS2, actin promoter, ubiquitin promoter, thiolase promoter.

According to another embodiment of the invention, the vectors comprise an inducible promoter. Examples of inducible promoters suitable for the constructs and methods according to the present invention include but are not limited to the lac promoter or xylose inducible promoter Optionally, the present expression vectors will also contain sequences necessary for the termination of transcription and for stabilizing the mRNA, and may thus contain one or more transcription termination sequences. The term "transcription termination sequence" encompasses a control sequence at the end of a transcriptional unit, which signals 3' processing and termination of transcription. Additional regulatory elements, such as transcriptional or translational enhancers, may be incorporated in the expression construct.

The expression constructs of the invention may further include an origin of replication that is required for maintenance and/or replication in a specific cell type. One example is when an expression construct is required to be maintained in a bacterial cell as an episomal genetic element (e.g. plasmid or cosmid molecule). Preferred origins of replication include, but are not limited to the f1-ori, colE1 ori, and Gram+ bacteria origins of replication.

The expression construct may optionally comprise a selectable marker gene. As used herein, the term "selectable marker gene" includes any gene, which confers a phenotype on a cell in which it is expressed to facilitate the identification and/or selection of cells which are transfected or transformed with an expression construct of the invention. Suitable markers may be selected from markers that confer antibiotic or herbicide resistance or visual markers. Examples of selectable marker genes include genes encoding neomycin phosphotransferase (nptII), hygromycin phosphotransferase (hpt) or Basta. Further examples of suitable selectable marker genes include resistance genes against ampicillin (AmpR), tetracydine (TcR), kanamycin (KanR), phosphinothricin, and chloramphenicol or thiamphenicol (CAT). Other suitable marker genes provide a metabolic trait, for example manA. Visual marker genes may also be used and include for example beta-glucuronidase (GUS), luciferase and Green Fluorescent Protein (GFP).

Construction of suitable vectors containing one or more of the above listed components and including the desired coding and control sequences employs standard ligation techniques. Isolated plasmids or nucleic acid fragments are cleaved, tailored, and religated in the form desired to generate the plasmids required.

5. Host Cells

According to one aspect, the present invention relates to a host cell comprising a polynucleic acid or a vector as defined herein.

The term "host cell" refers to those cells capable of growth in culture and capable of expressing a polynucleic acid as defined herein and thus capable of producing and secreting a fusion protein as defined herein. The host cells of the present invention encompass in vitro cell cultures and include prokaryotic cells. Particular embodiments relate to micro-organisms. Particular examples of host cells which may be used in accordance with the present invention include bacterial cells.

It shall be noted that the term "host cell" is intended to include all forms of the life cycle of the host cell such as spores.

In particular embodiments, the host cells envisaged in the context of the invention are bacterial cells, in particular gram positive bacterial cells. The term "Gram-positive bacteria" is intended to include the art-recognized definition of this term. Gram-positive bacteria include, but are not limited to, *Bacillus, Geobacillus, Clostridium, Streptococcus, Cellulomonas, Corynebacterium, Lactobacillis, Lactococcus, Oenococcus* and *Eubacterium*.

According to a particular embodiment of the present invention, said host cell is a gram-positive bacterial cell member of the class Clostridia, more preferably a member of the genus *Clostridium*.

Most particularly, Clostridia strains are envisaged which are amenable to genetic manipulation such as but not limited to *C. acetobutylicum, C. sporogenes, C. beijerinckii* etc.

The selection of the host cell may be determined by the envisaged application. Most particularly, the invention is applicable to strains for which secretion of polypeptides of interest is problematic.

In one embodiment said host cell is a member of the group comprising solventogenic, i.e. solvent producing, Clostridia strains. Particularly preferred host cells according to this embodiment of the invention are solvent-producing Clostridia strains selected from the group comprising *C. acetobutylicum*, for instance *C. acetobutylicum* strain ATCC824, and *C. beijerinckii*, for instance *C. beijerinckii* strain ATCC17778.

In another embodiment said host cell is a member of the group comprising sporogenic bacteria, such as but not limited to bacteria of the genus *Bacillus, Clostridium* (more particularly for therapeutic applications, where administration of spores is of interest). Particularly preferred host cells according to this embodiment of the invention are Clostridia strains selected from the group comprising *C. sporogenes*, for instance *C. sporogenes* strain DSM767, and *C. acetobutylicum*, for instance *C. acetobutylicum* strain ATCC824.

The polynucleic acid molecules or vectors according to the invention may either be integrated into the genome of the host cell or it may be maintained in some form extrachromosomally.

More in particular, host cells may be transformed with the expression vectors of this invention and cultured in conventional nutrient media modified as is appropriate for inducing promoters, selecting transformants or amplifying genes. "Transformation" means introducing nucleic acid into an organism so that the nucleic acid is replicable, either as an extrachromosomal element or by chromosomal integration. Methods used herein for transformation of the host cells are well known to a skilled person. The culture conditions, such as temperature, pH and the like, are those previously used with the host cell selected for expression, and will be apparent to the ordinarily skilled artisan.

6. Methods for Producing and Secreting Polypeptides

In another aspect, the present application is directed to a method for the production and secretion by a host cell, preferably a bacterial host cell, of at least one heterologous or homologous polypeptide of interest in a biologically active form comprising introducing into said host cell of a polynucleic acid or a vector according to the invention under conditions effective to cause expression of the encoded fusion protein, wherein the encoded fusion protein is secreted by the host cell into the environment of said host cell.

During secretion a signal peptide is preferably cleaved from said fusion protein such that the fusion protein is released in the host environment (e.g. a culture medium). In another aspect, a protease target sequence introduced in the linker connecting the carrier domain to the functional domain as defined herein, and the protein of interest is cleaved by protease(s) to release in the host environment the protein of interest cleaved from the remaining fusion protein.

Preferably said host cell is a bacterial host cell as defined above.

The environment of said host cell is intended to refer to the place wherein said bacterium in grown. In one embodiment the environment of said bacterium may be a culture medium wherein said bacterium is grown. In another embodiment the environment of said bacterium may be a tissue of a living being, e.g. a human or animal tissue, in particular in the case of therapeutic applications contemplated in the present invention.

The present invention also relates to the use of a polynucleic acid, a vector or a host cell according to the invention, for the production and secretion of a polypeptide of interest in a biologically active form.

The invention further relates to the use of a carrier domain as defined herein for controlling the secretion of a polypeptide of interest, preferably a polypeptide as defined herein. In this context it shall be noted that the term "controlling the secretion" is intended to encompass generation, induction, and/or the improvement of secretion. More particularly, the invention is directed to the use of a carrier domain as defined herein fused to a signal peptide as defined herein, for controlling the secretion of a polypeptide of interest, preferably a polypeptide as defined herein, by a host cell.

With "improvement of secretion" is meant that the amount of polypeptide of interest secreted is higher, and preferably at least 2.5, or 5 or 10% higher, than the amount obtained in the case no carrier domain fused to a signal peptide as defined herein, is used to control the secretion.

7. Non-Therapeutic Applications

In one embodiment the polypeptide of interest is an enzyme as defined herein. In such embodiment, the present application is directed to various non-therapeutic uses of a fusion protein according to the invention.

In one embodiment, said polypeptide of interest preferably is an enzyme as defined herein.

In another embodiment, said polypeptide of interest preferably is a plant cell wall degrading enzyme as defined herein, and even more preferred a cellulase as defined herein.

In more specific embodiments, the invention provides for the use of a polynucleic acid, a vector or a host cell according to the invention, for the production and secretion of a plant cell wall-degrading enzyme as defined herein, and even more preferred a cellulase of microbial origin, as defined above, preferably of bacterial origin, and for example from a bacteria of the genus Alteromonadaceae, e.g. *Saccharophagus degradans* strain 2-40, of the genus *Thermomonospora*, e.g., from *T. fusca*, of the genus Cellulomonadaceae e.g. *C. fimi*, of the genus Clostridia, e.g. from *Clostridium thermocellum, Clostridium cellulolyticum, Clostridium acetobutylicum*. In another embodiment the cellulase is of fungal origin, and for example from a fungus of the genus Neocallimastigomycota, e.g. from *N. patriciarum* or *Orpinomyces* sp strain PC-2.

Even more preferred the present invention relates to the use of a polynucleic acid, a vector or a host cell according to the invention, for the production and secretion of a cellulase of *C. cellulolyticum*, of *C. thermocellum*, of *C. acetobutylicum* or of *Saccharophagus degradans*, as defined above in a biologically active form.

In a particularly preferred embodiment the invention relates to the use of a polynucleic acid, a vector or a host cell according to the invention, for the production and secretion of the cellulase Cel48F of *C. cellulolyticum*.

In a particularly preferred embodiment the invention relates to the use of a polynucleic acid, a vector or a host cell according to the invention, for the production and secretion of the cellulase Cel9G of *C. cellulolyticum*.

In yet another particularly preferred embodiment the invention relates to the use of a polynucleic acid, a vector or a host cell according to the invention, for the production and secretion of the cellulase Cel5H of *Saccharophagus degradans*.

8. Therapeutic Applications

A further aspect of the invention relates to the therapeutic application of the carrier constructs and host cells comprising carrier constructs according to the present invention.

In particular embodiments the polypeptide of interest is a therapeutic protein as defined herein. In such embodiments, the present application is preferably directed to various therapeutic uses of a fusion protein according to the invention.

It has been shown that the avascular hypoxic/necrotic regions in solid tumors which are difficult to reach with classical therapies provide a suitable environment for the growth and proliferation of obligate, anaerobic bacteria. More particularly it has been demonstrated upon intravenous injection, clostridial spores are dispersed throughout the body, but only those that encounter the hypoxic environment of a solid tumour go on to germinate and multiply (Mose and Mose, 1964; Carey et al, 1967). Thus clostridial spores are ideal carriers for drug delivery in cancer. However, the major problem encountered with drug-delivery by clostridia is the level of secreted proteins. The present invention provides a way to address this problem, by providing a system which allows secretion of fusion proteins comprising a polypeptide of interest by micro-organisms such as Clostridia.

Accordingly, the invention provides for the use of a polynucleic acid, a vector or a host cell according to the invention, for the production and secretion of a therapeutic protein as defined herein. In particular embodiments the therapeutic protein is selected from the group comprising therapeutic enzymes, cytokines, and antibodies.

According to particular embodiments, the present invention relates to the use of a polynucleic acid encoding a fusion protein comprising a therapeutic protein according to the invention and a host cell comprising the polynucleic acid, for the production and secretion of cytokines, more particularly cytokines in a biologically active form, by recombinant micro-organisms.

More particularly the invention relates to the use of a polynucleic acid encoding a fusion protein comprising a therapeutic protein according to the invention and a host cell comprising the polynucleic acid, for the production and secretion of a cytokine selected from the group comprising IL-2, IL-12, GM-CSF and TNF-α by recombinant micro-organisms.

In further embodiments the therapeutic protein is a pro-drug converting enzyme.

In a further aspect, the invention relates to a pharmaceutical composition comprising a therapeutically active amount of polynucleic acid, vector or host cell, more particularly of a recombinant micro-organism according to the invention and at least one pharmaceutically acceptable carrier, i.e. for instance one or more pharmaceutically acceptable carrier substances and/or additives, e.g., buffers, carriers, excipients, stabilisers, etc. More particularly, the recombinant micro-organism is in the form of a bacterial spore, most particularly a *Clostridium* spore.

The term "therapeutically effective amount" as used herein means that amount of polynucleic acid, vector or host cell (i.a. recombinant micro-organism or spore thereof) that elicits the biological or medicinal response in a tissue, system, animal or human that is being sought by a researcher, veterinarian, medical doctor or other clinician.

The term "pharmaceutically acceptable" as used herein is consistent with the art and means compatible with the other ingredients of a pharmaceutical composition and not deleterious to the recipient thereof. Suitable pharmaceutically acceptable carriers are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

The pharmaceutical preparations can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage or amount of an polynucleic acid, vector or host cell as defined herein used depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to a polynucleic acid, vector or host cell as defined herein.

The preparation of the pharmaceutical compositions can be carried out in a manner known per se. To this end, the polynucleic acid, vector or host cell as defined herein together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human medicine.

The pharmaceutical composition according to the invention is preferably administered parenterally, for example subcutaneously, intramuscularly or intravenously in the form of solutions for injection or infusion. Other suitable administration forms are, for example, microcapsules, implants or rods.

Suitable carriers for the preparation of solutions, for example of solutions for injection, for example, water, physiological sodium chloride solution, alcohols such as ethanol, glycerol, polyols, sucrose, invert sugar, glucose, mannitol, vegetable oils, etc. It is also possible to lyophilize the host cell as defined herein and to use the resulting lyophilisates, for example, for preparing preparations for injection.

Suitable carriers for microcapsules, implants or rods are, for example, copolymers of glycolic acid and lactic acid.

In a particularly preferred embodiment, the pharmaceutical composition according to the invention is injectable. The composition may for instance be administered (injected) at a tumor site. Such application enables the delivery of the product contained in the pharmaceutical composition, i.e. polynuclucic acid, vector, host cell as defined herein, to the tumor cells. The delivered compounds, e.g. polynuclucic acid, vector, host cell as defined herein, to the tumor cells, is preferably injected one or more times a week during months, or even years.

In another particularly preferred embodiment, the pharmaceutical composition according to the invention can be delivered using reservoirs, such as for instance micropumps, in order to deliver the product, i.e. polynuclucic acid, vector, host cell as defined herein, to the tumor in cells in cancer types.

In addition, the invention is directed to a polynucleic acid, a vector, or a host cell according to the invention for use as a medicament. In other words, the invention also relates to the use of a polynucleic acid, a vector, or a host cell according to the invention as a medicament.

In a further embodiment, the invention relates to a polynucleic acid, a vector, or a host cell according to the invention for treating cancer. More particularly, the invention relates to the use of a polynucleic acid, a vector, or a host cell according to the invention for the preparation of a medicament for treating cancer.

In an example, recombinant clostridia bacteria engineered as disclosed herein can be used for cancer treatment, as Clostridia spores are able to germinate and develop in the neighborhood of tumors.

Various types of cancer can be treated in accordance with the present invention. The invention therefore also relates to a method of treating cancer in a subject in need thereof comprising introducing a host cell according to the invention in said subject, and preferably at a tumor site in said subject. Practically, the present invention thus comprises the introduction of a recombinant host cell, capable of expressing a polynucleic acid according to the invention at the tumor site in a subject in need thereof; and thus capable of producing a polypeptide of interest according to the invention at the tumor site in the host. The present invention thus provides the delivery of the product, i.e. a therapeutic protein, such as e.g. a cytokine, contained in a polynucleic acid, vector, host cell or pharmaceutical composition as defined herein, selectively into tumor cells. Based on the fact that solid tumors, at some stage of their development, are characterized by severe hypoxia and necrosis, such transfer system is considered as a valuable anti-cancer strategy. Such a therapy is believed to circumvent normal tissue toxicity and to improve tumor cell kill, as the result of its direct delivery of the product to the tumor.

The invention will be further understood with reference to the following non-limiting examples.

EXAMPLES

The practice of the present invention will employ, unless otherwise indicated, conventional techniques used in recombinant DNA technology, molecular biology, biological testing, and the like, which are within the skill of the art. Such techniques are explained fully in the literature.

Example 1

Secretion of Heterologous and Toxic Cellulases

This example illustrates the secretion of polypeptides of interest, in particular the cellulases, by *C. acetobutylicum* in accordance with the present invention. Various constructions were made and the most relevant of these are schematically represented on FIG. 1.

In a first construct, the polynucleic acid encoding the cellulase Cel48F obtained from *C. cellulolyticum*, was fused to a polynucleic acid encoding a carrier domain and comprising the CBM3a module, the X module (Xc), and the cohesin 1 module of CipC of *C. cellulolyticum* The construct further contains the signal peptide of the CipC scaffolding protein of *C. cellulolyticum*. Suitable linker sequences are used to link the different modules to one another.

In a second construct, the polynucleic acid encoding the cellulase Cel48F obtained from *C. cellulolyticum*, was fused to a polynucleic acid encoding a carrier domain and comprising the CBM3a and one X module (Xc) of CipC of *C. cellulolyticum* The construct further contains the signal peptide of the CipC scaffolding protein of *C. cellulolyticum*. Suitable linker sequences are used to link the different modules to one another.

In a third construct, the polynucleic acid encoding the cellulase Cel9G obtained from *C. cellulolyticum*, was fused to a polynucleic acid encoding a carrier domain and comprising the CBM3a and one X module (Xc) of CipC of *C. cellulolyticum*. The construct further contains the signal peptide of the CipC scaffolding protein of *C. cellulolyticum*. Suitable linker sequences are used to link the different modules to one another.

As controls, a construct was made comprising a polynucleic acid encoding cellulase Cel48F obtained from *C. cellulolyticum* and the signal peptide of the CipC scaffolding protein of *C. cellulolyticum* but without a carrier domain or and X module and another construct was made comprising a polynucleic acid encoding cellulase Cel9G obtained from *C. cellulolyticum* and the signal peptide of the CipC scaffolding protein of *C. cellulolyticum* fused to a polynucleic acid encoding the CBM3a module but without the X module. In addition, similar constructs were made with and without the c-terminal dockerin domain.

The various constructs were constructed using Overlap Extension PCR technique, and cloned in the shuttle expression vector pSOS952, that confers resistance to the antibiotic erythromycin, thereby generating the plasmids pSOS952-CBM-Xc-Cohesin-48F; pSOS952-CBM-Xc-48F and pSOS952-CBM-Xc-9G, respectively. The constructs were checked by sequencing, and methylated in vivo. The methylated vectors were subsequently used to electrotransform *C. acetobutylicum* strain ATTC 824.

It was shown that *C. acetobutylicum* strains bearing the first two constructs secreted a fusion protein containing the cellulase Cel48F in their growth medium in amounts of about 0.5 mg/L. Furthermore, also the *C. acetobutylicum* strains bearing the third constructs also secreted a fusion protein containing the cellulase Cel9G in its growth medium in amounts of about 0.5 mg/L. However, in the absence of the carrier domain (CBM+X module) the constructs comprising only a cellulase with a signal sequence were toxic to the cells (i.e. no secretion). The presence of a c-terminal dockerin domain did not change this.

These results show that, when the cellulases Cel9G or Cel48F are fused by genetic engineering to the signal sequence and to two modules (CBM and X) or three modules (CBM, X and cohesin) of the scaffoldin CipC from *C. cellulolyticum*, the chimeric enzymes are produced and secreted in the medium by *C. acetobutylicum*. The secretion yields of the engineered cellulases were estimated to be around 0.3-0.5 mg/L. These values are based on activity of the culture supernatant on cellulose. Alternatively, the concentration of the heterologous cellulases in the culture supernatant was also estimated by polyacrylamide gel electrophoresis analysis under denaturing conditions followed by densitometric analyses).

The presence of the CBM has the advantage of rapidly allowing the protein of interest to be purified from the supernatant of the culture on crystalline cellulose column.

Example 2

Secretion of a Heterologous and Toxic Cellulase According to the Invention Using Multiple X Modules This is another example illustrating the secretion of polypeptides of interest, in particular cellulases, by *C. acetobutylicum* in accordance with the present invention. Various constructions were made and are schematically represented on FIG. 1 (lower panel), wherein modules obtained from different scaffolding proteins were used.

In one construct the polynucleic acid encoding the cellulase Cel9G obtained from *C. cellulolyticum*, was fused to a polynucleic acid encoding a carrier domain and comprising the CBM3a obtained from the CipC protein of *C. cellulolyticum* and one X module (Xa) obtained from the CipA protein of *C. acetobutylicum*. The construct further contains the signal peptide of the CipC scaffolding protein of *C. cellulolyticum*. Suitable linker sequences are used to link the different modules to one another.

In a fifth construct the polynucleic acid encoding the cellulase Cel9G obtained from *C. cellulolyticum*, was fused to a polynucleic acid encoding a carrier domain and comprising the CBM3a obtained from the CipC protein of *C. cellulolyticum* and the first (Xa) and the second (Xa') X modules of CipA of *C. acetobutylicum*. The construct further contains the signal peptide of the CipC scaffolding protein of *C. cellulolyticum*. Suitable linker sequences are used to link the different modules to one another.

These constructs were constructed using Overlap Extension PCR technique, and cloned in the shuttle expression vector pSOS952, that confers resistance to the antibiotic erythromycin, thereby generating the plasmids pSOS952-CBM-Xa-9G and pSOS952-CBM-Xa-Xa'-9G respectively. The constructs were checked by sequencing, and methylated in vivo and in vitro. The methylated vectors were subsequently used to electrotransform *C. acetobutylicum* strain ATTC 824

It was shown that *C. acetobutylicum* strains bearing these two constructs secreted a fusion protein containing the cellulase Cel9G in their growth medium in relevant amounts. These results also showed that when the cellulase Cel9G is fused by genetic engineering to the signal sequence and to the CBM of the scaffoldin CipC from *C. cellulolyti-* *cum*, and to one or two X modules from CipA of *C. acetobutylicum* chimeric enzymes are produced and secreted in the medium by *C. acetobutylicum*. This indicates that the X modules from CipA of *Clostridium acetobutylicum* also have carrier properties with respect to secretion by *C. acetobutylicum*. The Applicants also further showed that using more than one X module had beneficial effects on secretion. The secretion yield of the fusion cellulases was estimated at 1.9 and 3.5 mg/L for the strains carrying the vectors pSOS952-CBM-Xa-9G and pSOS952-CBM-Xa-Xa'-9G, respectively. The concentration of the heterologous cellulases in the culture supernatant was also estimated by polyacrylamide gel electrophoresis analysis under denaturing conditions followed by densitometric analyses.

Example 3

Figure 2:
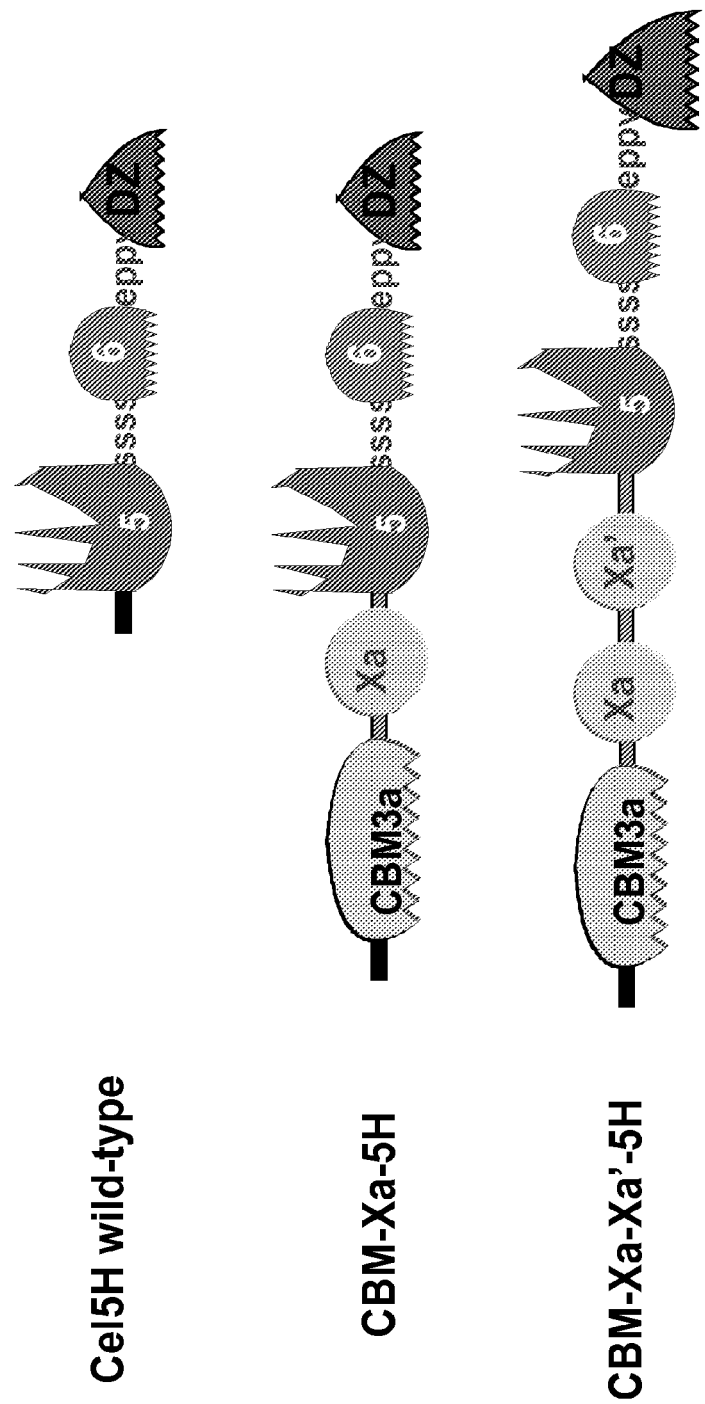
FIG. 2 is a schematic representation of different constructs according to particular embodiments of the invention. The constructs comprise a polypeptide of interest (cellulase "Cel5H") fused to a carrier domain and a signal sequence. The carrier domain comprises a carbohydrate binding module (CBM3a) from a cellulosomal scaffolding protein fused to one or two X modules (Xa). Cellulase Cel5H comprises a glycoside hydrolase family 5 domain ("5"), a polyserine linker ("sss"), a carbohydrate-binding module family 6 domain ("6"), a glutamic acid-proline-rich region ("eppv") and a C-terminal domain identified by the present inventors as a putative carbohydrate-binding module ("DZ").

Improvement of the Secretion of a Heterologous Cellulase According to the Invention This is another example illustrating the secretion of polypeptides of interest, in particular a cellulase from *Saccharophagus degradans*, by *C. acetobutylicum* in accordance with the present invention. Various constructions were made and are schematically represented on FIG. 2, wherein modules obtained from different scaffolding proteins were used.

In a first construct, the synthetic polynucleic acid adapted to *C. acetobutylicum* codon bias and encoding the cellulase Cel5H from *Saccharophagus degradans*, was fused to a polynucleic acid encoding a carrier domain and comprising the CBM3a module, the first (Xa) and the second (Xa') X modules obtained from the CipA protein of *C. acetobutylicum* and the signal peptide of the CipC scaffolding protein of *C. cellulolyticum*. Suitable linker sequences are used to link the different modules to one another.

The domain structure of the native Cel5H polypeptide can be outlined as GH5-PSL-CBM6-EPR-DZ, wherein GH5 stands for its glycoside hydrolase family 5 domain, PSL for the polyserine linker, CBM6 for carbohydrate-binding module family 6 domain, EPR for the glutamic acid-proline-rich region and, without being limited to this interpretation, DZ represents a C-terminal domain identified by the present inventors as a putative carbohydrate-binding module.

This construct was constructed using Overlap Extension PCR technique, and cloned in the shuttle expression vector pSOS952, that confers resistance to the antibiotic erythromycin, thereby generating the plasmid pSOS952-CBM-Xa-Xa'-5H. The constructs were checked by sequencing, and methylated in vivo and in vitro. The methylated vector was subsequently used to electrotransform *C. acetobutylicum* strain ATTC 824.

Figure 3:
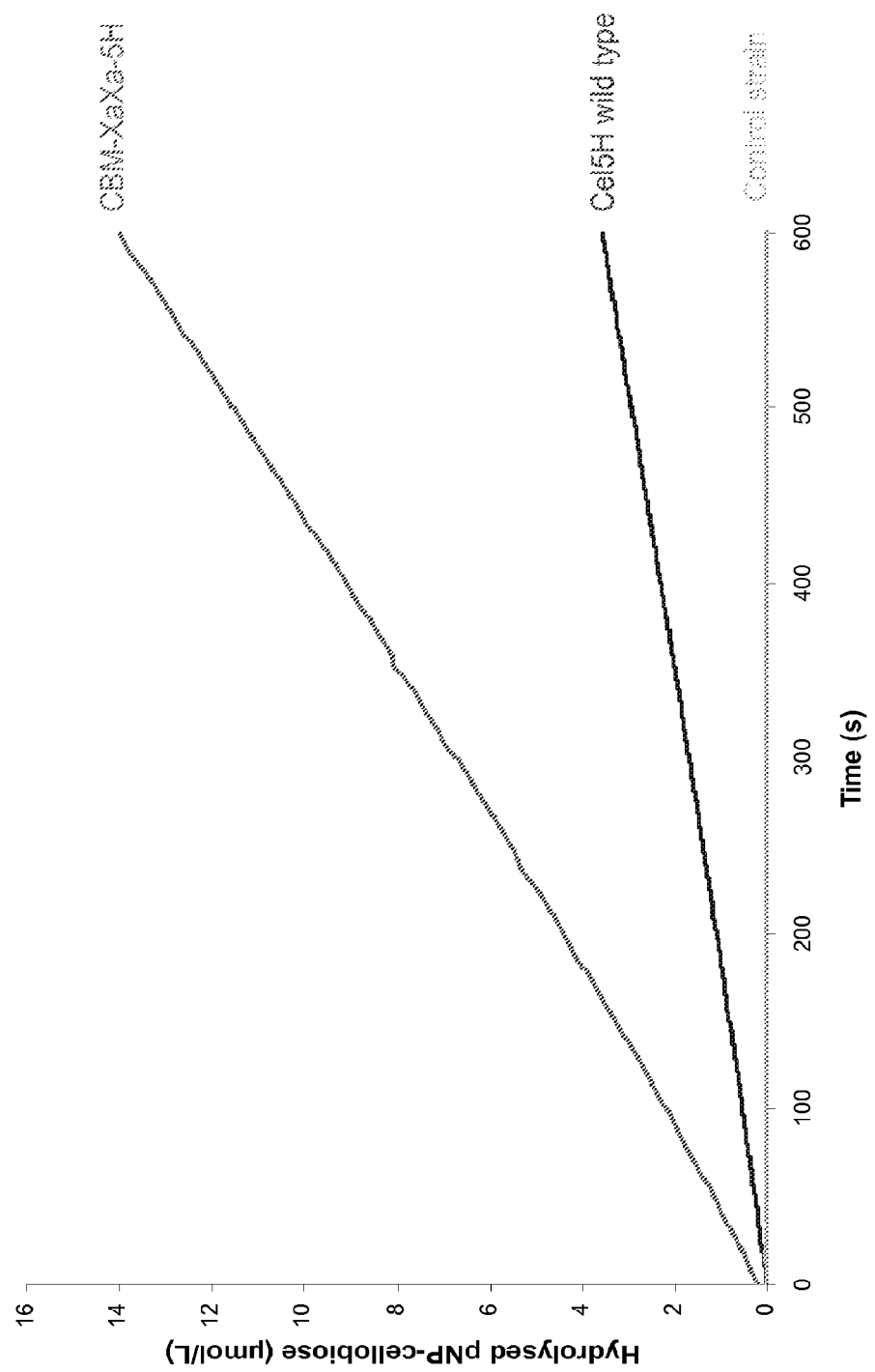
FIG. 3 demonstrates the secretion of wild-type Cel5H and Cel5H fused to a carrier domain, compared to a control strain. The carrier domain encompasses a carbohydrate binding module (CBM3a) from a cellulosomal scaffolding protein fused to two hydrophilic domains (Xa). The activity of the culture supernatant was measured on the soluble substrate para-nitrophenyl-cellobiose.

The secretion by *C. acetobutylicum* of the wild-type Cel5H protein appended with the signal peptide of the scaffoldin CipC from *C. cellulolyticum* was 0.5-0.9 mg/L (values based on the activity of the culture supernatant on para-nitrophenyl-cellobioside). However, *C. acetobutylicum* strains bearing the two constructs encoding the fusion protein comprising the Cel5H protein linked to the carrier domain secreted a fusion protein containing the cellulase 5H in their growth medium in significantly higher amounts, more particularly up to 6.1 mg/L (value based on the activity of the culture supernatant on para-nitrophenyl-Cellobioside, see FIG. 3). These results again demonstrate that when the heterologous (i.e. non-Clostridial) cellulase Cel5H is fused by genetic engineering to the signal sequence and to the CBM of the scaffoldin CipC from *C. cellulolyticum*, and to one or two X modules from CipA of *C. acetobutylicum* chimeric enzymes are produced and secreted in the medium by *C. acetobutylicum*.

Example 4

Demonstration of the Activity of the Fusion Proteins According to the Invention on Cellulose Using molecular biology techniques the DNA encoding the different protein constructs described in Examples 2 and 3 was amplified and cloned in an *E. coli* expression vector (pET22b(+), Novagen). The resulting vector was used to transform the *E. coli* strain BL21 (DE3) (Novagen). In all cases, six His codons were grafted at the C-terminus extremity of the recombinant proteins to facilitate their purification on Nickel resin (Ni-NTA, Qiagen).

The recombinant strains were grown in Luria Bertani medium and the expression of the cloned genes was triggered using IPTG as the inducer. The synthesis of the recombinant proteins was verified by denaturing polyacrylamide gel electrophoresis (SDS-PAGE). The cultures were centrifuged and the harvested cells were broken in a French press.

The recombinant proteins were purified by loading the crude extract on Ni-NTA (Qiagen), and elution of the protein of interest using increasing concentrations of imidazolium. Purification was achieved using FPLC Q-sepharose (Hitrap Q HP resin, GE Healthcare).

Figure 4:
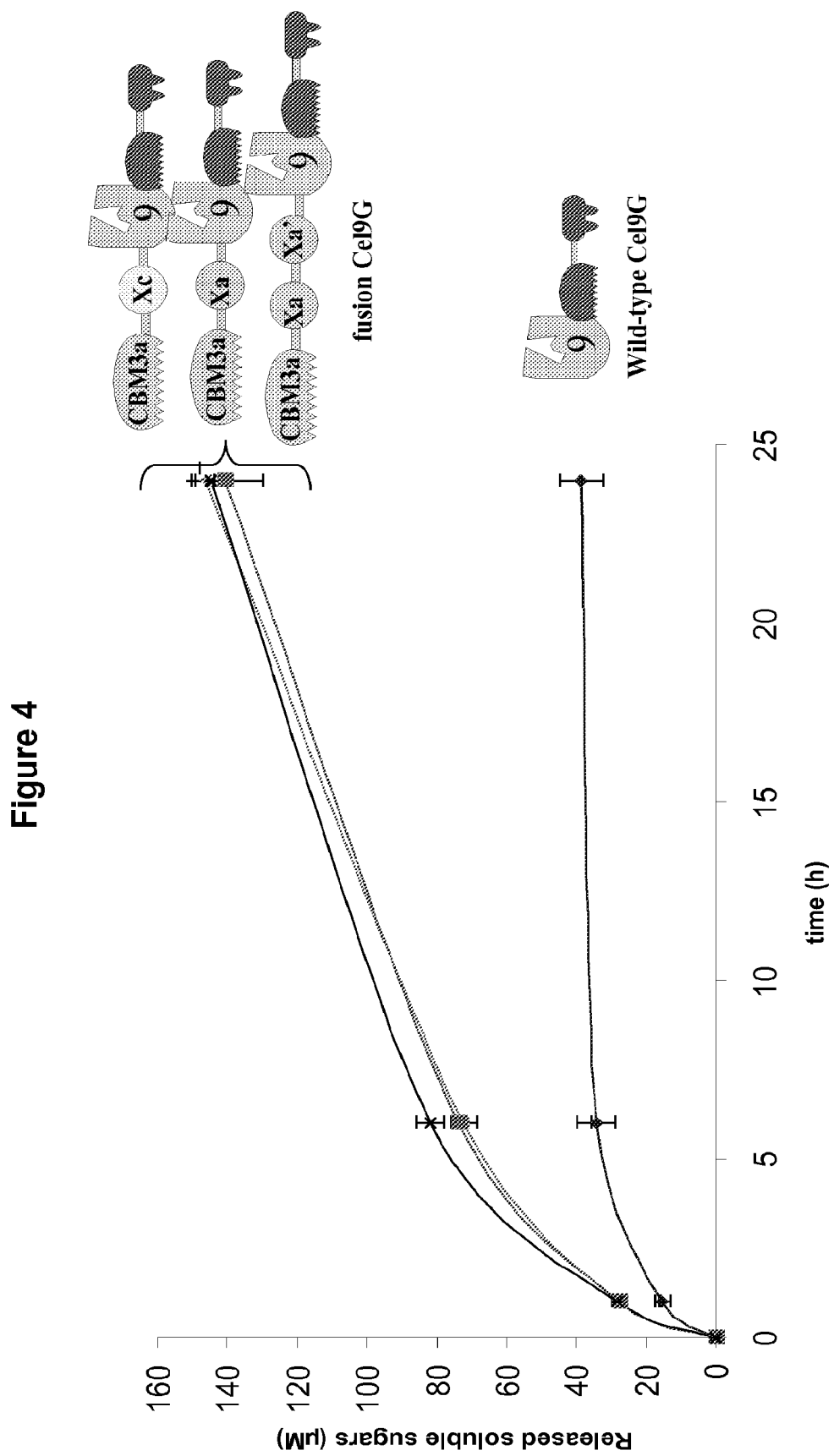
FIG. 4 demonstrates the activity of different proteins including the fusion proteins according to particular embodiments of the invention on cellulose: activity of proteins comprising Cel9G on crystalline cellulose Avicel compared to wild-type Cel9G. The legend is as in FIG. 1.
Figure 5A:
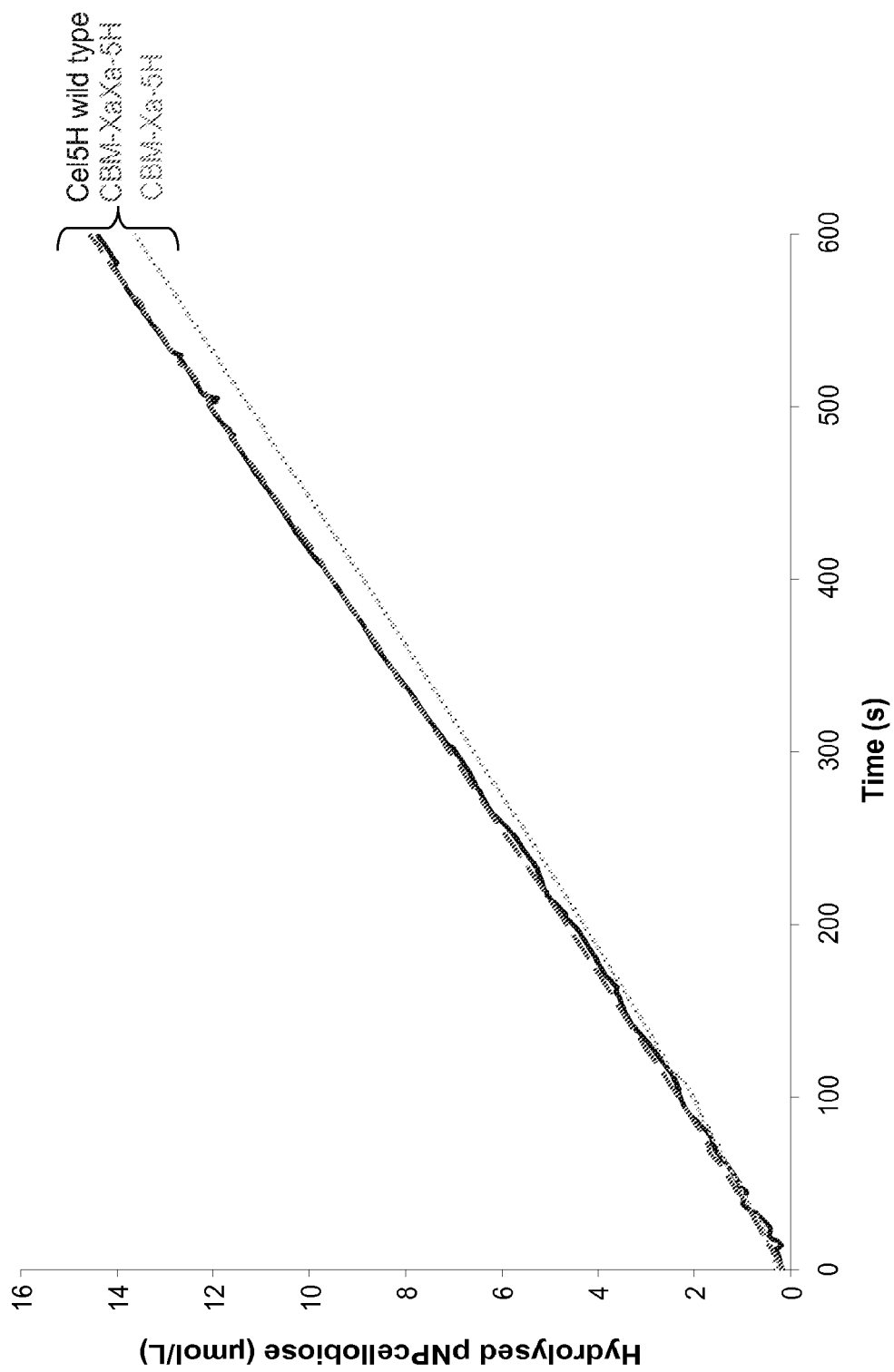
FIG. 5 demonstrates the activity of different proteins including the fusion proteins according to particular embodiments of the invention on different celluloic substrates; (a) activity of proteins comprising Cel5H on soluble substrate para-nitrophenyl-cellobiose; wild-type Cel5H (full line), fusion with one X module (CBM-Xa-5H; dotted line), fusion protein with two X modules (CBM-Xa-Xa-5H, dashed line) (b) activity of proteins comprising cel5H on crystalline cellulose Avicel.
Figure 5B:
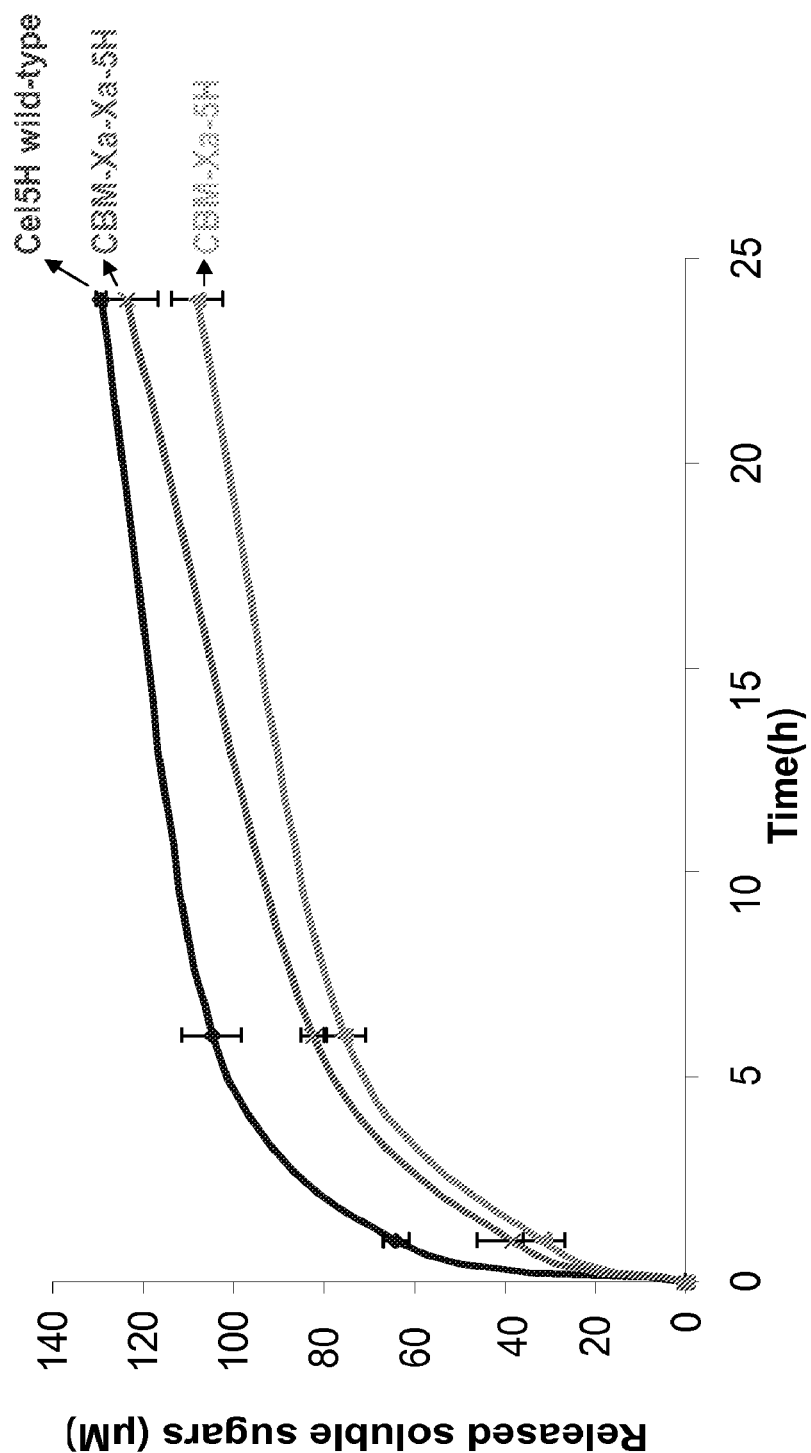

Activity of the purified enzymes was tested on Avicel (microcrystalline cellulose) using standard conditions (37° C.). The results are illustrated in FIGS. 4 and 5b. Alternatively, the activity was measured on para-nitrophenyl-cellobioside and the results are presented in FIG. 5a.

Example 5

Secretion of a Therapeutic Protein

This is another example illustrating the secretion of polypeptides of interest, in particular a therapeutic protein interleukine 2 from rat, by *C. acetobutylicum* in accordance with the present invention. A construction is made wherein modules obtained from different scaffolding proteins are used.

In the construct the polynucleic acid encoding the interleukine 2 from rat (IL2), is fused to a polynucleic acid encoding a carrier domain comprising the CBM3a obtained from the CipC protein of *C. cellulolyticum* and the first (Xa) and the second (Xa') X modules of CipA of *C. acetobutylicum*. The construct further contains the signal peptide of the CipC scaffolding protein of *C. cellulolyticum*. Suitable linker sequences are used to link the different modules to one another.

The construct is constructed using Overlap Extension PCR technique, and cloned in the shuttle expression vector pSOS952, that confers resistance to the antibiotic erythromycin, thereby generating the plasmid pSOS952-CBM-Xa-Xa'-IL2. The construct is checked by sequencing, and methylated in vivo. The methylated vector iss subsequently used to electrotransform *C. acetobutylicum* strain ATTC 824.

It is shown that *C. acetobutylicum* strains bearing this construct secretes a fusion protein containing the rat interleukine 2 in their growth medium in relevant amounts. These results also show that when the rat interleukine 2 is fused by genetic engineering to the signal sequence and to the CBM of the scaffoldin CipC from *C. cellulolyticum*, and to two X modules from CipA of *C. acetobutylicum*, the chimeric protein is produced and secreted in the medium by *C. acetobutylicum*. This indicates that the CBM from CipC of *C. cellulolyticum* and the X modules from CipA of *C. acetobutylicum* also have carrier properties with respect to secretion by *C. acetobutylicum* of a therapeutic protein from a mammal. The fusion protein containing the rat IL2 iss purified from the culture supernatant by loading the external medium on a column of crystalline cellulose Avicel. The fusion protein is eluted from Avicel using purified water (milliQ water), and mass spectrometry analyses as well as N-terminal micro-sequencing confirm the integrity of the purified recombinant protein.

The invention claimed is:

1. A polynucleic acid encoding a fusion protein which comprises in this order:
   at least one signal peptide;
   a carrier domain comprising a carbohydrate binding module (CBM) of a cellulosomal scaffolding protein fused to one, two, or three X modules of a cellulosomal scaffolding protein wherein at least one X module is the X2 module of the CipA scaffolding protein of *C. acetobutylicum*;
   at least one peptide linker; and
   at least one polypeptide of interest;
   wherein said peptide linker links the carrier domain to the polypeptide of interest, and
   wherein said polypeptide of interest comprises an enzyme.

2. The polynucleic acid of claim 1, wherein said fusion protein comprises two or three X modules.

3. The polynucleic acid of claim 1, wherein said signal peptide is the signal peptide of the CipC scaffolding protein of *C. celluloyticum* or the signal peptide of the CipA scaffolding protein of *C. acetobutylicum*.

4. The polynucleic acid of claim 1, wherein said fusion protein comprises a carbohydrate binding module of type-3a (CBM3a).

5. The polynucleic acid of claim 1, wherein said enzyme is a cell wall degrading enzyme.

6. The polynucleic acid of claim 1, wherein said enzyme is a cellulase.

7. The polynucleic acid of claim 6, wherein said enzyme is a cellulase of *C. celluloyticum*.

8. The polynucleic acid of claim 6, wherein said enzyme is *C. celluloyticum* Cel48F or *C. celluloyticum* Cel9G.

9. The polynucleic acid of claim 1, wherein said enzyme is cellulase Cel5H of *S. degradans* strain 2-40.

10. A recombinant micro-organism comprising the polynucleic acid encoding a fusion protein according to claim 1, wherein the recombinant micro-organism is capable of secreting said enzyme when cultured under conditions effective to cause expression of the fusion protein.

11. The recombinant micro-organism of claim 10, wherein said micro-organism is from the class of *Clostridia*.

12. The recombinant micro-organism of claim 10, wherein said micro-organism is from a *Clostridium* strain selected from the group consisting of *C. acetobutylicum* and *C. beijerinckii*.

13. The recombinant micro-organism of claim 10, wherein said signal peptide is the signal peptide of the CipC scaffolding protein of *C. celluloyticum* or the signal peptide of the CipA scaffolding protein of *C. acetobutylicum*.

14. The recombinant micro-organism of claim 10, wherein said fusion protein comprises a carbohydrate binding module of type-3a (CBM3a).

15. The recombinant micro-organism of claim 10, wherein said enzyme is a cell wall degrading enzyme.

16. The recombinant micro-organism of claim 10, wherein said enzyme is a cellulose of C. cellulolyticum.

17. The recombinant micro-organism of claim 10, wherein said enzyme is cellulase Cel5H of S. degradans strain 2-40.

18. A method for the production and secretion of an enzyme of interest comprising the steps of:
   introducing the polynucleic acid encoding the fusion protein according to claim 1 into a recombinant micro-organism, wherein the polypeptide of interest comprises the enzyme of interest; and
   culturing said recombinant micro-organism under conditions effective to cause expression of the fusion protein, wherein the enzyme of interest is secreted by the recombinant micro-organism into the culture medium of said recombinant micro-organism.

19. The polynucleotide of claim 1, wherein the carbohydrate binding module is fused to one X module of a cellulosomal scaffolding protein, wherein said X module is the X2 module of the CipA scaffolding protein of C. acetobutylicum.

20. The recombinant micro-organism of claim 10, wherein the fusion protein comprises a carbohydrate binding module fused to one X module of a cellulosomal scaffolding protein, wherein said X module is the X2 module of the CipA scaffolding protein of C. acetobutylicum.

* * * * *